United States Patent
Chen et al.

(10) Patent No.: US 10,383,940 B2
(45) Date of Patent: *Aug. 20, 2019

(54) COPPER-CYSTEAMINE AND METHODS OF USE

(71) Applicant: BOARD OF REGENTS, THE UNIVERSITY OF TEXAS SYSTEM, Austin, TX (US)

(72) Inventors: Wei Chen, Arlington, TX (US); Lun Ma, Arlington, TX (US)

(73) Assignee: THE BOARD OF REGENTS, THE UNIVERSITY OF TEXAS SYSTEM, Austin, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/049,755

(22) Filed: Jul. 30, 2018

(65) Prior Publication Data
US 2018/0339047 A1    Nov. 29, 2018

Related U.S. Application Data

(63) Continuation of application No. 15/421,292, filed on Jan. 31, 2017, now Pat. No. 10,064,942, which is a continuation of application No. 14/907,595, filed as application No. PCT/US2014/048557 on Jul. 29, 2014, now Pat. No. 9,593,131.

(Continued)

(51) Int. Cl.
| | | |
|---|---|---|
| A61K 41/00 | (2006.01) | |
| A61K 31/30 | (2006.01) | |
| A61K 51/04 | (2006.01) | |
| A61N 5/06 | (2006.01) | |
| A61N 5/10 | (2006.01) | |
| C07F 1/08 | (2006.01) | |
| C12N 13/00 | (2006.01) | |

(Continued)

(52) U.S. Cl.
CPC .......... *A61K 41/0057* (2013.01); *A61K 31/30* (2013.01); *A61K 51/025* (2013.01); *A61K 51/0478* (2013.01); *A61N 5/062* (2013.01); *A61N 5/10* (2013.01); *C07F 1/08* (2013.01); *C12N 13/00* (2013.01); *G21K 4/00* (2013.01); *A61N 2005/0661* (2013.01); *A61N 2005/109* (2013.01); *A61N 2005/1087* (2013.01); *A61N 2005/1089* (2013.01)

(58) Field of Classification Search
CPC ................ A61K 31/30; A61K 2300/00; A61K 41/0057; A61K 51/0478; A61N 2005/0661; A61N 2005/1087; A61N 2005/1089; A61N 2005/109; A61N 5/062; A61N 5/10; C07F 1/08; C12N 13/00; G21K 4/00
See application file for complete search history.

(56) References Cited

PUBLICATIONS

Lun MA et al., "New Cu-cysteamine complex: structure and optical properties," J. Materials Chen. C, 2, pp. 4239-4246 (2014).

(Continued)

*Primary Examiner* — Savitha M Rao
(74) *Attorney, Agent, or Firm* — FisherBroyles LLP; Anthony Dovale

(57) ABSTRACT

Structure and luminescence properties of a new Cu-Cysteamine (Cu-Cy) crystal material are provided. The crystal structure of the Cu-Cy is determined by single crystal X-ray diffraction. It is found that the compound crystallizes in the monoclinic space group C2/c and cell parameters are a=7.5510(4) Å, b=16.9848(7) Å, c=7.8364(4) Å, β=104.798 (3)°. The new Cu-Cy crystal material of the invention is also useful for treatment of cancer.

16 Claims, 25 Drawing Sheets

Related U.S. Application Data

(60) Provisional application No. 61/932,112, filed on Jan. 27, 2014, provisional application No. 61/859,460, filed on Jul. 29, 2013.

(51) Int. Cl.
 *G21K 4/00* (2006.01)
 *A61K 51/02* (2006.01)

(56) References Cited

PUBLICATIONS

Parish RV, et al., "Five-Coordinate Sulfur in a Polymeric Copper(I) Thiolate Complex," Angew. Chem. Int Ed. Eng., 36 No. 3 (1997).
Matrana BA et al., "Polarography of Copper (111)-(1) Cysteamine-Cystamine Systems," Analytical Letters, 4(7), pp. 437-444 (1971).
Bharara MS et al., "Synthesis and X-ray crystal structures of dinuclear hydrogen-bonded cadmium and lead 2-aminoethanethiolates," Polyhedron 24, pp. 865-871 (2005).
Written Opinion of the International Searching Authority; PCT/US2014/048557; dated Nov. 20, 2014.
Extended European Search Report pursuant to Rule 62 EPC, dated Mar. 15, 2017.

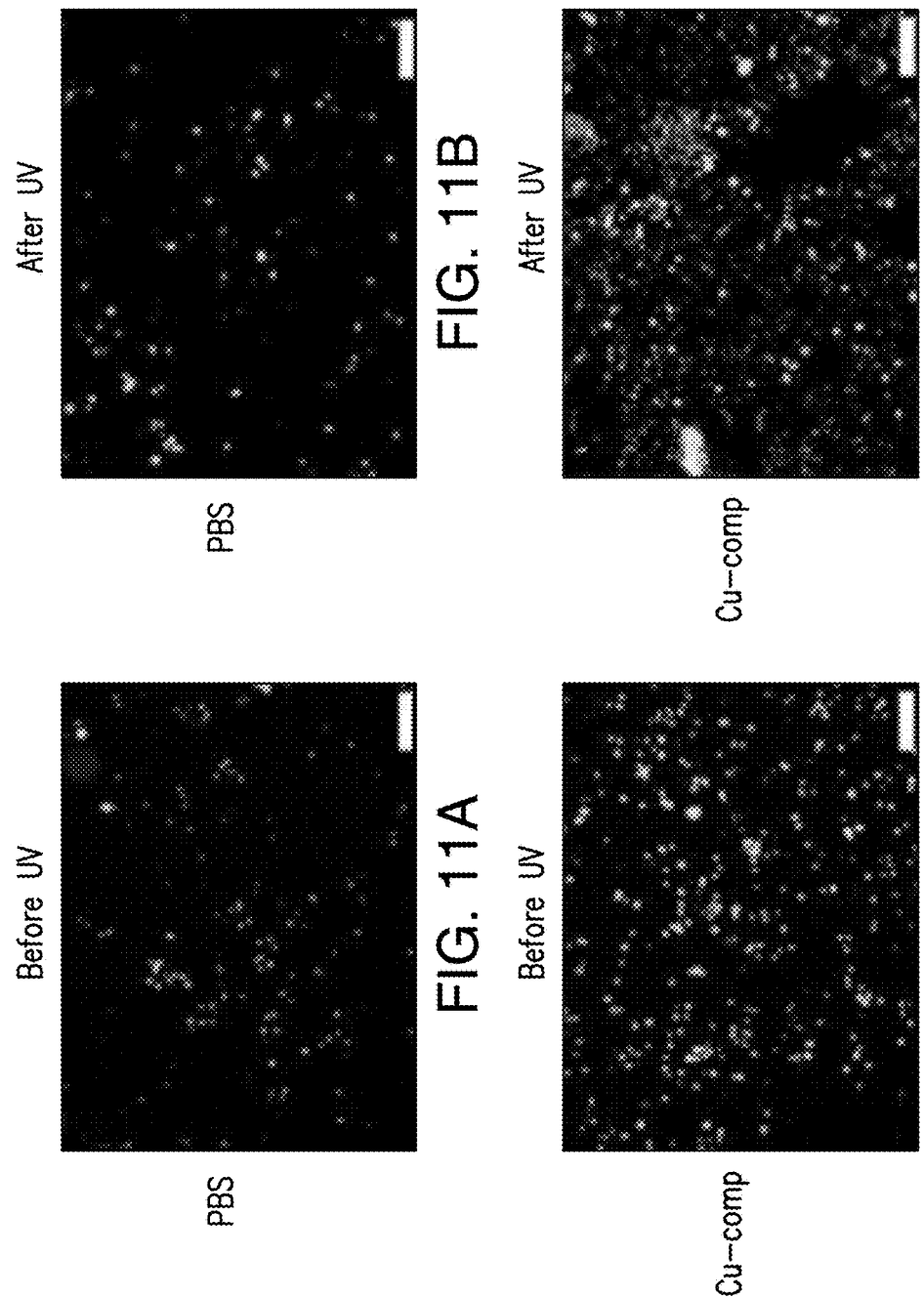

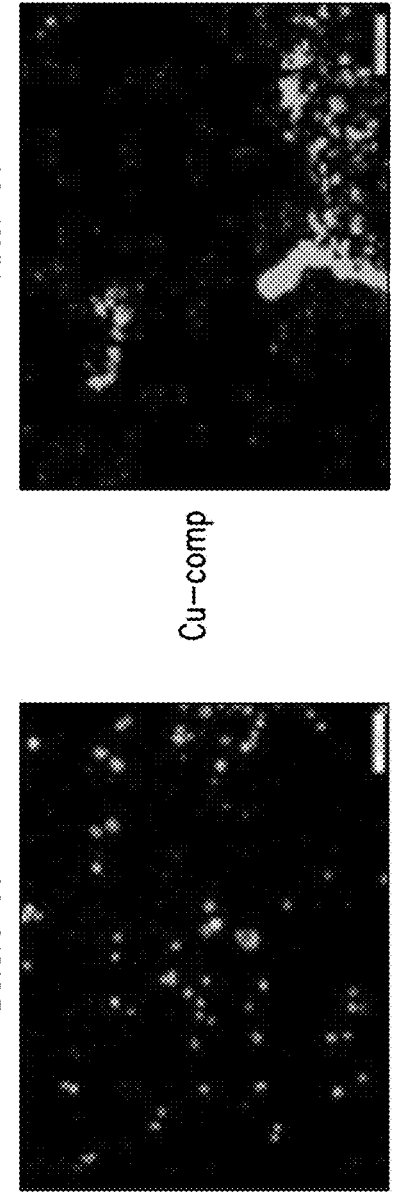
FIG. 12A  FIG. 12B  FIG. 12C  FIG. 12D

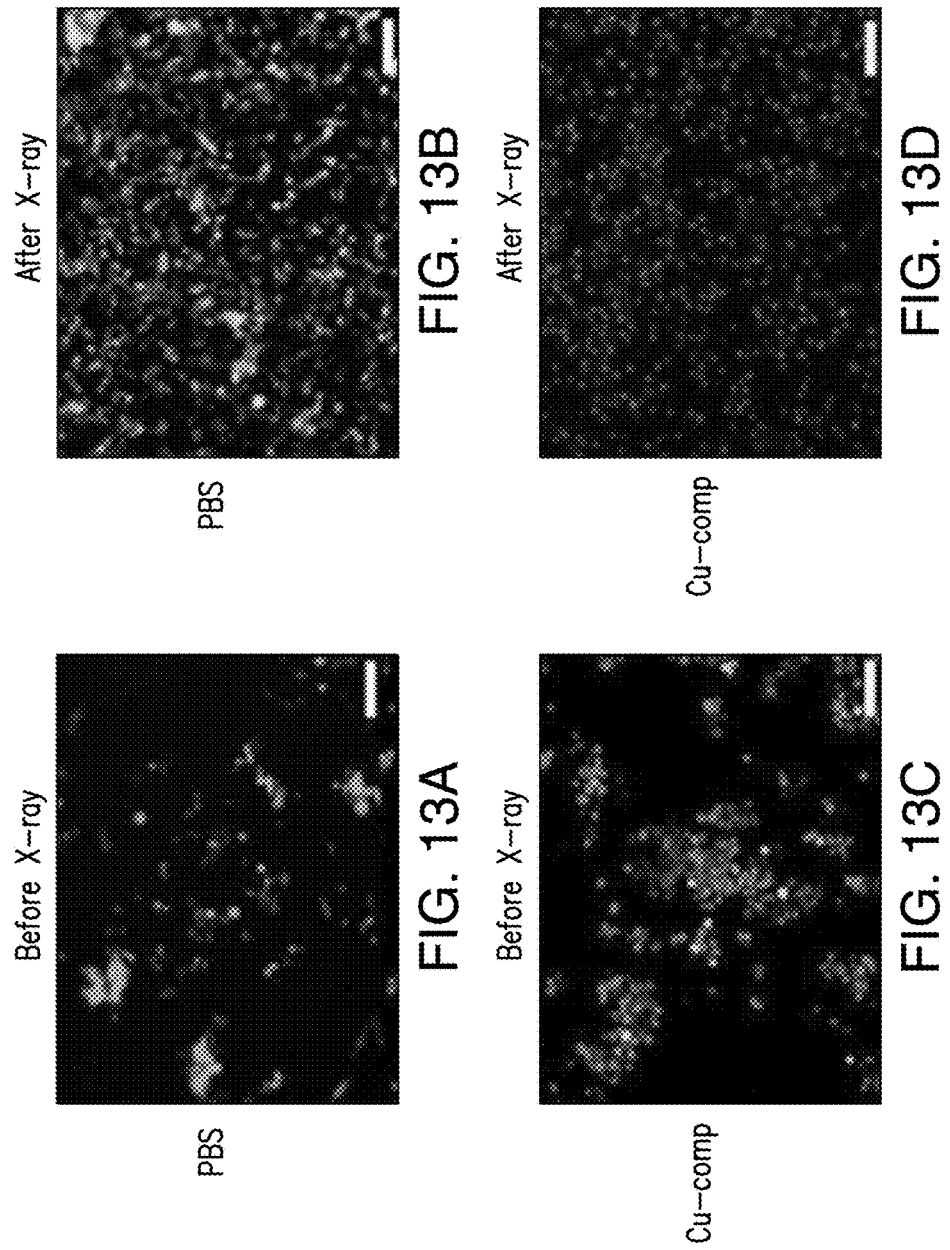

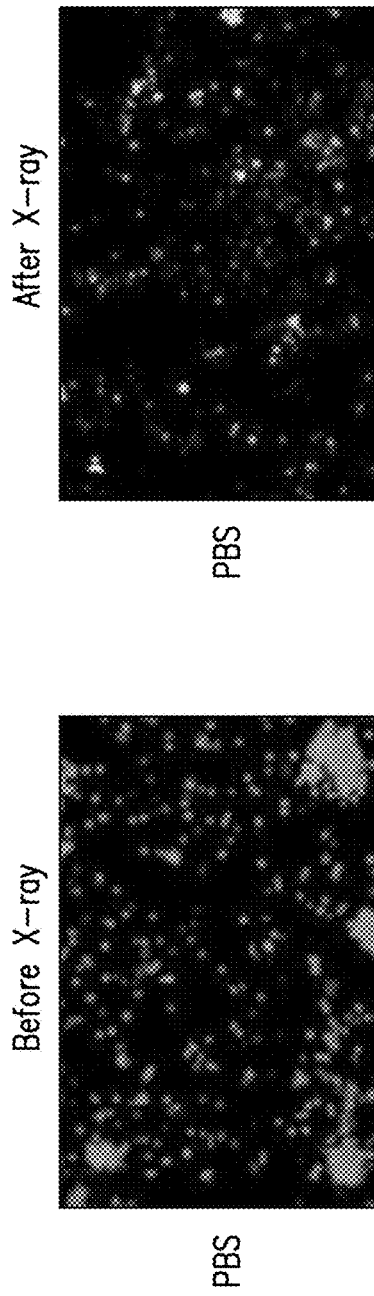
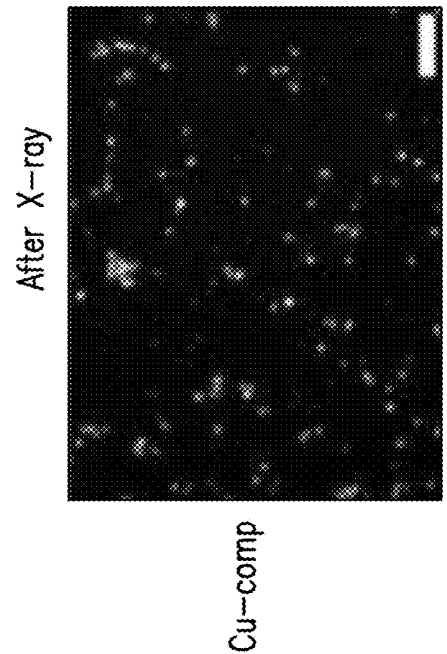
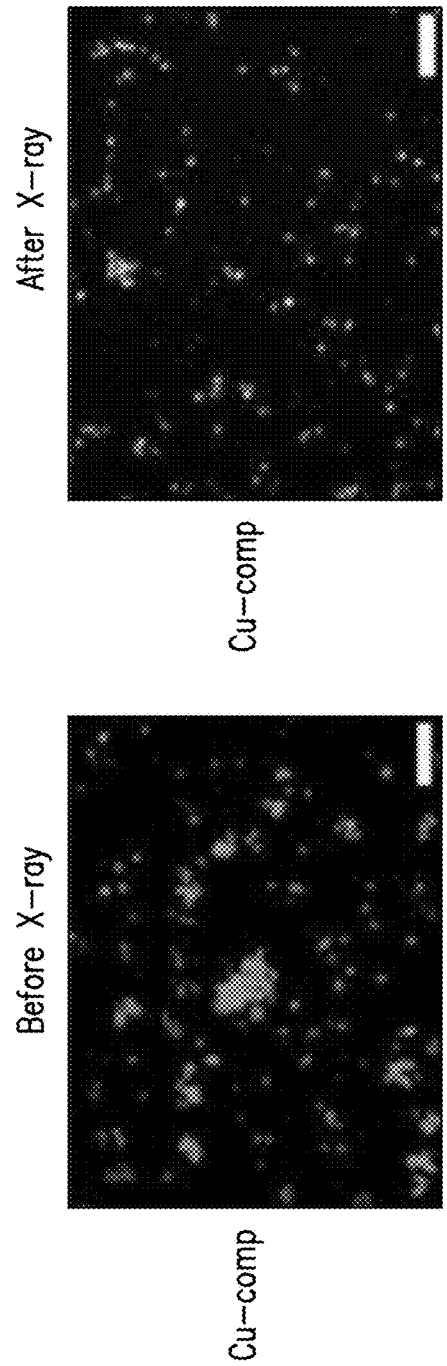
FIG. 14A  Before X-ray  PBS
FIG. 14B  After X-ray  PBS
FIG. 14C  Before X-ray  Cu-comp
FIG. 14D  After X-ray  Cu-comp

COPPER-CYSTEAMINE AND METHODS OF USE

CROSS REFERENCE TO RELATED APPLICATIONS

This application claims the benefit of Provisional Application Ser. No. 61/859,460, filed on Jul. 29, 2013, and Provisional Application Ser. No. 61/932,112, filed Jan. 27, 2014, the entire disclosure of which is incorporated herein by reference in its entirety.

FIELD OF THE INVENTION

A novel copper-cysteamine (Cu-Cy) complex and its properties are disclosed. Further disclosed are compositions and materials which comprise the Cu-Cy complex. Yet further disclosed are methods of using the Cu-Cy complex, inter alia, as a treatment of cancer and as a means for detecting sources of radiation. Still further disclosed are methods for preparing various morphologies of the disclosed Cu-Cy complex.

BRIEF DESCRIPTION OF THE DRAWINGS

The following drawings illustrate by way of example and not limitation. For the sake of brevity and clarity, every feature of a given structure is not always labeled in every figure in which that structure appears.

FIG. 10A: Bright-field image, FIG. 10B: Fluorescence image excited by 405 nm, FIG. 10C: Fluorescence image excited by 360 nm, FIG. 10D: a photo combination of FIG. 10B and FIG. 10C. The scale bar is always 50 µm.

FIGS. 11A-11D depict the comparison of UV light (350 nm) destruction on human hepatocellular liver cells (HEPT) without (top row, FIG. 11A and FIG. 11B) and with (bottom row, FIG. 11C and FIG. 11D) Cu-Cy crystals. Significant cell death is only observed in the case of Cu-Cy crystals and UV irradiation. The scale bar is always 100 µm.

FIGS. 12A-12D depict the comparison of UV light (350 nm) destruction on human breast cancer (MCF-7) cells without (top row, FIG. 12A and FIG. 12B) and with (bottom row, FIG. 12C and FIG. 12D) Cu-Cy crystals. Significant cell death is only observed in the case of Cu-Cy crystals and UV irradiation. The scale bar is always 100 µm.

FIGS. 13A-13D depict the comparison of X-ray (2 Gy) destruction on human breast cancer (MCF-7) cells without (top row, FIG. 14A and FIG. 14B) and with (bottom row, FIG. 14C and FIG. 14D) Cu-Cy crystals. Significant cell death has been observed in the presence of Cu-Cy crystals and X-ray irradiation. The scale bar is always 100 µm.

FIGS. 14A-14D depict the comparison of X-ray (2 Gy) destruction on human prostate cancer (PC3) cells without (top row, FIG. 14A and FIG. 14B) and with (bottom row, FIG. 14C and FIG. 14D) Cu-Cy crystals. Significant cell death is only observed in the case of Cu-Cy crystals and X-ray irradiation. The scale bar is always 100 µm.

DETAILED DESCRIPTION

Figures 1A, 1B, 1C:
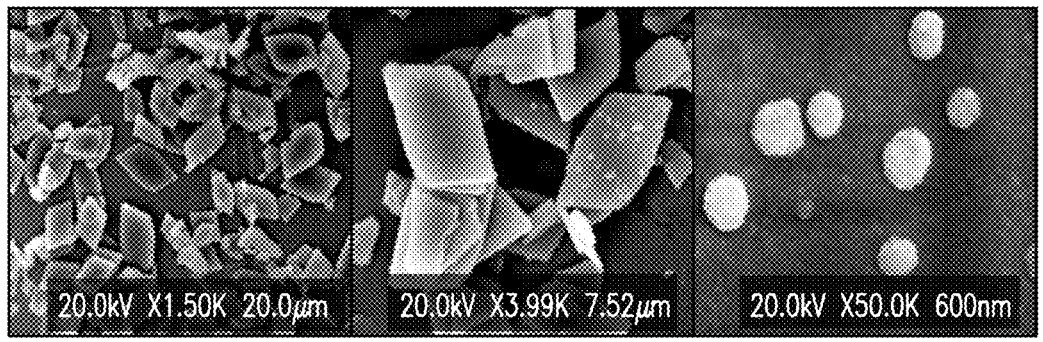
FIGS. 1A-1F depict the SEM (FIG. 1A, FIG. 1B, and FIG. 1C) and HRTEM (FIG. 1D, FIG. 1E, and FIG. 1F) images of the disclosed Cu-Cy crystals. The inset in FIG. 1D is the electron diffraction pattern of the crystals.

The materials, compounds, compositions, articles, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

All percentages, ratios and proportions herein are by weight, unless otherwise specified. All temperatures are in degrees Celsius (° C.) unless otherwise specified.

The terms "a" and "an" are defined as one or more unless this disclosure explicitly requires otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Values expressed as "greater than" do not include the lower value. For example, when the "variable x" is defined as "greater than zero" expressed as "0<x" the value of x is any value, fractional or otherwise that is greater than zero.

Similarly, values expressed as "less than" do not include the upper value. For example, when the "variable x" is defined as "less than 2" expressed as "x<2" the value of x is any value, fractional or otherwise that is less than 2.

"Optional" or "optionally" means that the subsequently described event or circumstance can or cannot occur, and that the description includes instances where the event or circumstance occurs and instances where it does not.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

Compound

Disclosed herein is a copper-cysteamine (Cu-Cy) having the formula:

$$Cu_3Cl(SR)_2$$

wherein R is —$CH_2CH_2NH_2$. The terms "copper-cysteamine," "Cu-Cy material," "Cu-Cy complex," "Cu-Cy," "disclosed material," "disclosed complex," "disclosed compound" and the like are used herein interchangeably throughout the present disclosure to represent the above-identified chemical compound. As depicted in the appended Figures, the compound can have various forms depending upon the method of preparation employed by the formulator. The present disclosure does not exclude any morphology, crystalline form and the like.

The disclosed complex exhibits emission peaks at 607 nm and 633 nm and X-ray luminescence at 633 nm. The Cu-Cy materials are stable in aqueous solution, as well as other common solvents.

The disclosed Cu-Cy materials can be formed in crystals in micrometer or millimeter size. In addition to the micron-sized crystals, smaller crystals from tens to several hundred nanometers have also been prepared. The methods for producing the copper-complex materials can be accomplished without the protection afforded by an inert atmosphere, for example, nitrogen or argon blanketing or the need for hazardous organic solvents. After simply mixing and heating the copper and organic reactants in water, the Cu-Cy crystals are formed and isolated from water solution as precipitation. The product can be then washed with water and ethanol as more specifically described in the examples. Sonication helps cleaning the products but is likely to break the crystals into small pieces.

Example 1

Preparation of the Disclosed Cu-Cy Compound

Copper(II) chloride dihydrate (99.99%), 2-mercaptoethylamine hydrochloride (Cysteamine hydrochloride or Cys, 98%) and Sodium hydroxide (98%) were purchased from Sigma (USA). All the chemicals were used as received. Deionized (DI) water was used as the reaction solvent without further purification.

$CuCl_2 \cdot 2H_2O$ (0.460 g, 2.698 mmol,) was dissolved in DI water followed by addition of cysteamine (0.636 g, 8.244 mmol). With excessive cysteamine, the $Cu^{2+}$ (Cu(II)) was completely reduced to $Cu^+$ (Cu(I)), expressed as $2HSR+Cu(II)=Cu(I)-SR+½ RSSR+2H^+$. After adjusting the pH value to 8 by adding a 2.5 M NaOH solution, the solution was stirred for about 2 hours at room temperature until the solution turned to deep violet as a result of oxidation. Without wishing to be limited by theory, an intermediate product consists of both Cu(I) and Cu(II) is proposed as the cause of the violet color and has the proposed formula $Cu(II)_2(SR)_2OCu(I)_4(SR)_4$.

The solution was then heated to its boiling temperature for 30 minutes. Crystals of $Cu_3Cl(SR)_2$ were precipitated from the solution and other reaction products were removed with the supernatant. The obtained $Cu_3Cl(SR)_2$ crystals were further centrifuged and washed using a mixture of DI water and ethanol (v/v=5:4) three times. Finally, the crystals were dried completely in a vacuum oven at room temperature overnight. Larger single crystals were obtained for longer time with no stirring. Without wishing to be limited by theory, the overall reaction to prepare the desired copper-cysteamine complex is as follows:

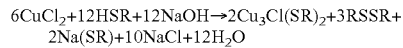

$$6CuCl_2+12HSR+12NaOH \rightarrow 2Cu_3Cl(SR)_2+3RSSR+2Na(SR)+10NaCl+12H_2O$$

wherein R is $-CH_2CH_2NH_2$.

X-ray photoelectron spectroscopy (XPS).

The Cu-Cy crystal powders were dispersed in ethanol and deposited on the surface of silver coated silicon wafer. After sample drying in a vacuum oven at 40° C. for a whole night, the XPS survey and quantification report were then carried out by using a Perkin-Elmer PHI 560 high performance spectrometer.

Luminescence Decay Lifetimes

The luminescence lifetimes were collected using a nanosecond optical parametric oscillator/amplifier (Spectra-Physics MOPO-730) operating at a 10 Hz repetition rate and tunable between 440 and 1800 nm. The output of the MOPO system was frequency doubled in a KDP crystal and directed onto the particles. Emission was collected at right angles to the excitation and focused into a ⅛ meter monochromator equipped with a standard photomultiplier tube.

Photoluminescence measurement.

The photoluminescence spectrum was measured by dispersing 0.1 mg Cu-Cy particles into 3 mL DI water and recorded by a Shimadzu RF-5301PC fluorescence spectrophotometer (Kyoto, Japan).

X-ray luminescence measurement.

The x-ray luminescence spectrum was measured in a light-proof X-ray cabinet equipped with optic fiber connection to an outside detector (QE65000 spectrometer, Ocean Optics Inc., Dunedin, Fla.). The X-ray Irradiation was performed using a Faxitron RX-650 (Faxitron X-ray Corp, IL, USA) at 90 kV with a 12 inch mm source-object distance and 5 mm distance optic fiber to object, at 135°. The luminescence spectra were recorded using a QE65000 spectrometer (Ocean Optics Inc., Dunedin, Fla.), connected to the X-ray chamber using a 0.6 mm core diameter optic fiber (P600-2-UV-V is, Ocean Optics Inc, Dunedin, Fla.), which has a probe head extended inside the X-ray chamber and positioned at 45° and 5 mm away from sample surface.

Quantum Yield (QY) Measurements.

The quantum yield measurement was carried out by using 10 mm fluorescence cuvettes with Shimadzu UV-2450 UV_vis spectrophotometer and RF-5301PC fluorescence spectrophotometer. Rhodamine B in water (quantum yield 0.31) was chosen as a standard. For each of Rhodamine B and Cu-complexes water solutions, five different concentrations and their corresponding measured integrated luminescence intensities ($\lambda exc=368$ nm) were recorded respectively and plotted in FIG. 9. Then linear fitting was applied (red lines) for each case and the quantum yield of Cu-Cy crystals in water was calculated according to: $\varphi=0.31*SlopeX/SlopeST$, where the subscript "X" and "ST" refer to the Cu-Cy and Rhodamine B respectively. In order to minimize re-absorption effects, absorbencies in the 10 mm fluorescence cuvette were always kept under 0.1.

Solid-state NMR Spectropscopy.

$^{13}C$ CP-MAS spectra were acquired on a Varian/Chemagnetics Infinityplus 9.4 T WB spectrometer and a 21.1 T Bruker Avance II spectrometer, respectively. All the $^{13}C$ CP-MAS spectra were obtained at room temperature with a contact time of 1 ms and a pulse delay of 5 s. The sample spinning rates were 8 and 10 kHz for (1) and cysteamine hydrochloride, respectively. $^{13}C$ chemical shifts were referenced externally to the resonance of the methylene carbon in adamantane (38.55 ppm relative to TMS)

Single crystal X-ray diffraction analysis.

In order to determine their structure, crystals of the invention suitable for single crystal X-ray diffraction were obtained using the seed growth method. A pale brown rod-like crystal of the invention, $(C_4H_{12}Cl_1Cu_3N_2S_2)$, having the approximate dimensions of 0.10×0.03×0.03 mm, coated with oil (Paratone 8277, Exxon), was collected onto the elongated aperture of a mounted MicroLoop E™ (diameter of the aperture: 100 microns; MiTeGen—Micro-technologies for Structural Genomics; USA).

The crystal was then mounted onto the goniometer head, which was quickly transferred to the cold stream of the Oxford cryo-jet. The mounted MicroLoop™ had previously been attached reusable goniometer bases consisting of stainless steel magnetic base and a copper post extending up from the stainless steel base. The MicroLoop™ is grabbed and securely hold in reusable goniometer bases without using epoxy.

All measurements were made on a Nonius KappaCCD 4-Circle Kappa FR540C diffractometer using monochromated Mo $K_\alpha$ radiation ($\lambda=0.71073$ Å) at $-100°$ C. An initial orientation matrix and cell was determined from 10 frames using φ scans and the data were measured using ω-scans. A total of 2662 reflections were collected. Cell parameters were initially retrieved using the COLLECT software, refined with the HKL DENZO and SCALEPACK software using 1355 observed reflections with $1.00°<\theta<30.03°$ (mosaicity: 0.428(3)°) from the data collection, and corresponded to a monoclinic cell. Data reductions were performed with the HKL DENZO and SCALEPACK software, which corrects for beam inhomogeneity, possible crystal decay, Lorentz and polarization effects. A multi-scan absorption correction was applied (SCALEPACK). The crystal structures were solved using the heavy atoms method (Patterson) and refined by full-matrix least-squares method on $F^2$ with SHELXL-2012. The non-hydrogen atoms were refined anisotropically. Hydrogen atoms were included at geometrically idealized positions and were not refined. The isotropic thermal parameters of these hydrogen atoms were fixed at 1.2 or 1.5 times that of the preceding carbon or nitrogen atom, respectively. Neutral atom scattering factors for non-hydrogen atoms and anomalous dispersion coefficients are contained in the SHELXL-2012 program. Further details for the determination of crystal structures are given in the supporting information. Molecular thermal ellipsoid plots were prepared using OLEX-2 for Windows.

The obtained Cu-Cy crystals are depicted in FIGS. 1A-1F with the use of scanning electron microscopy (SEM, Hitachi S-5000H system) and transmission electron microscopy (TEM, Hitachi 9500). The crystals are substantially rectangular shaped and in the sizes of micrometers (FIGS. 1A-1B). Small irregular pieces could be broken from larger crystals. At a higher magnification (FIG. 1C) agglomeration of nano-sized particles can been observed.

Figures 1D, 1E, 1F:
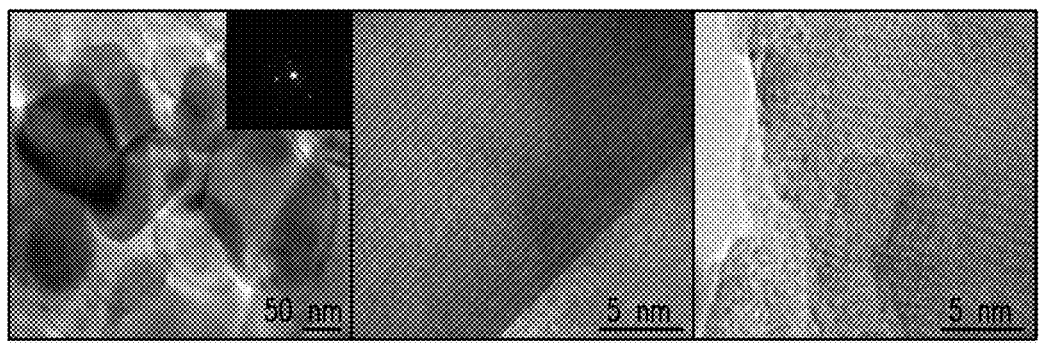
Figures 2A, 2B, 2C:
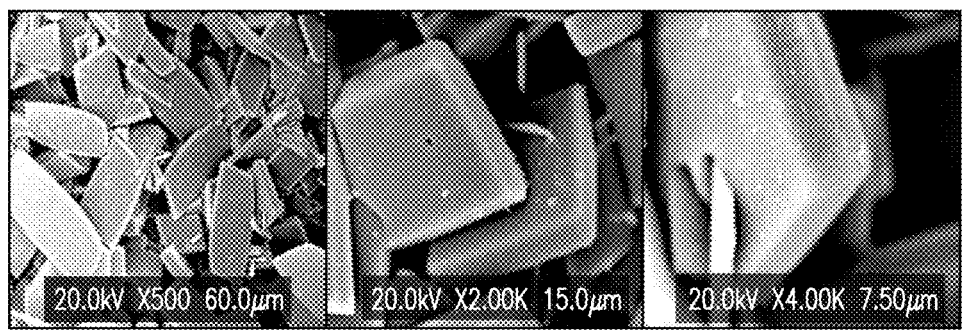
FIGS. 2A-2E depict SEM images (FIG. 2A, FIG. 2B, and FIG. 2C) of the disclosed Cu-Cy crystals obtained without stirring. High resolution SEM Images (FIG. 2D) and (FIG. 2E) show the edge area of the large crystal in the image (FIG. 2C).
Figures 2D, 2E:
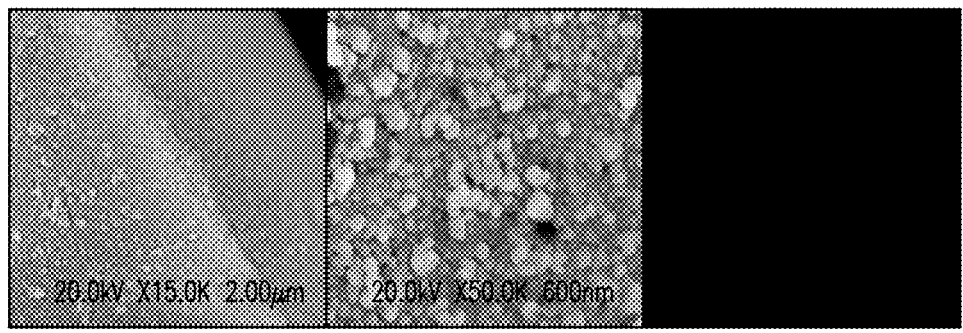

The smaller crystals were observed by TEM (FIG. 1D). Their electron diffraction pattern (inset, FIG. 1D) suggests that these small crystals are single crystals. Further, their high resolution TEM images display clear uniform lattice fringes (FIGS. 1E-1F). The HRTEM images demonstrate that these small crystals are highly crystalline and about 70 nm to 200 nm in size.

The microcrystal growth of the disclosed compound can be controlled by adjusting various factors, for example, choice of solvent, pH, temperature, etc. The disclosed Cu-Cy crystals can be obtained in the size of tens of micrometers in the absence of stirring. FIGS. 2A-2E provide supplementary SEM images.

Figure 3:
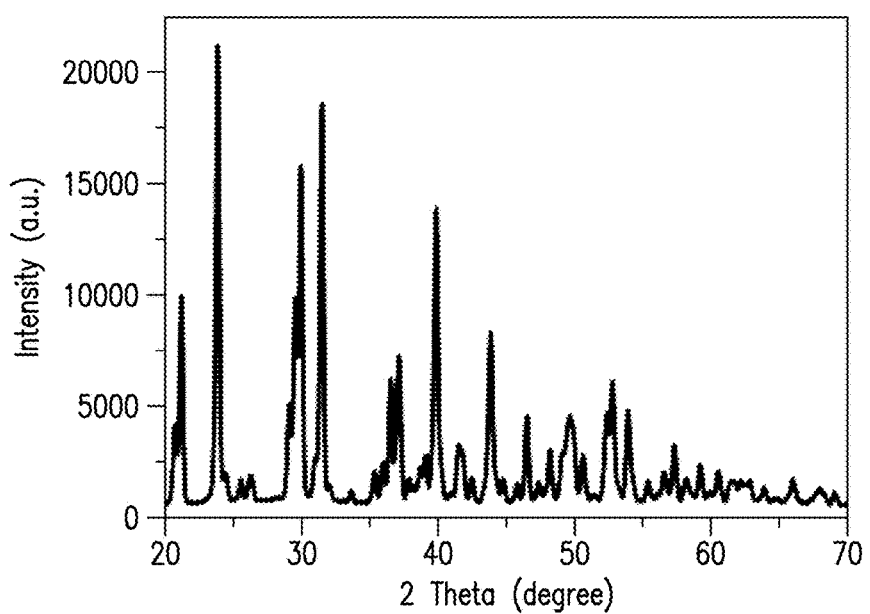
FIG. 3 depicts the XRD pattern of Cu-Cy crystals of the invention.

FIG. 3 represents the XRD pattern of the Cu-Cy crystal powder. The Cu-Cy crystals exhibited very sharp and intensive peaks. The lattice spacing measured from the high resolution TEM images are d=0.347 nm (FIG. 1E) and d=0.227 nm (FIG. 1F), which match the d values calculated from the XRD peaks at 25.70° (d=0.346 nm) and 39.94° (d=0.226 nm) respectively.

Figure 19:
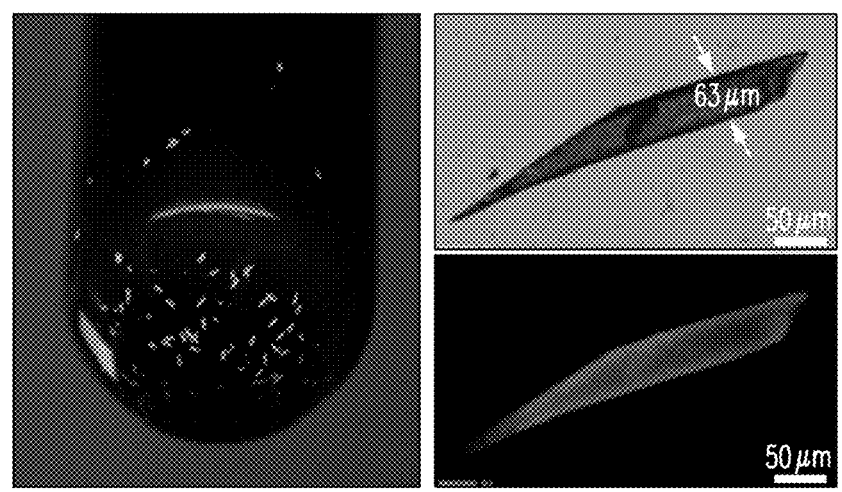
FIG. 19 depicts single crystals of the Cu-Cy of the invention, with size of about 60 µm×60 µm×450 µm. On the left are the crystals emitting red fluorescence excited by a UV lamp; on the right is one crystal imaged by an optical microscope (top right) and a microscope fluorescence image excited at 350 nm (bottom right).

The crystals used for single crystal XRD are shown in FIG. 19. The crystal size is approximately 60 μm×60 μm×450 μm and the luminescence spectra (FIG. 6) of these crystals are the same as that of the powder samples. The crystal structure of Cu-Cy (FIG. 20) was determined by single crystal X-ray diffraction. The compound crystallizes in the monoclinic space group C2/c and cell parameters are a=7.5510(4) Å, b=16.9848(7) Å, c=7.8364(4) Å, β=104.798(3)°. Its empirical formula is $Cu_3Cl(SR)_2$ with formula weight 378.38 g/mol. The new structure includes two different Cu atoms: Cu(1) and Cu(2), which bind to 4 and 3 other atoms respectively. The valence calculation shows they are both $Cu^+$ ions. In many examples of coordination structures, a thiolate sulfur atom typically binds less than 4 metal atoms. In the disclosed Cu-Cy crystals, the sulfur atom bridges 4 Cu atoms simultaneously.

Figure 21A:
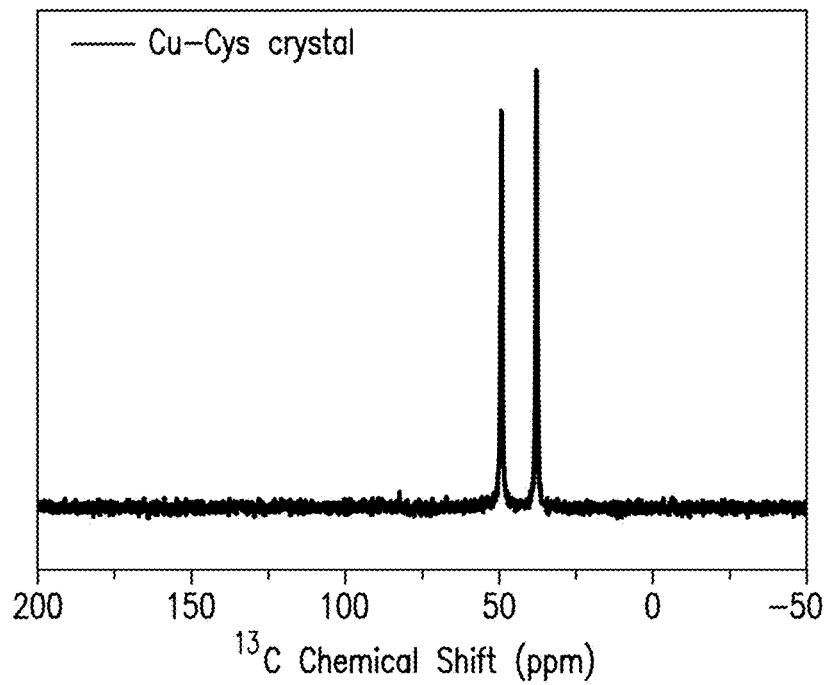
FIG. 21A depicts the $^{13}C$ CP-MAS spectra of the disclosed Cu-Cy crystals and FIG. 21B depicts the $^{13}C$ CP-MAS spectra of cysteamine.
Figure 21B:
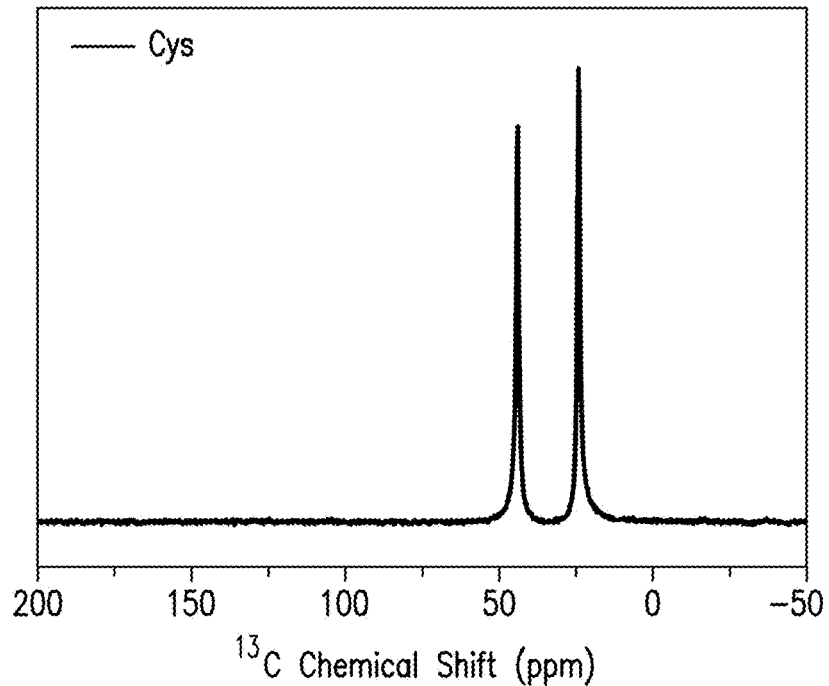

To further probe the oxidation state of Cu in the Cu-Cy, $^{13}C$ CP-MAS spectra of Cu-Cy and the ligand precursor (cysteamine hydrochloride) were acquired (FIGS. 21A-21B). For the ligand precursor ($HS-C(1)H_2-C(2)H_2-NH_2 \cdot HCl$), the isotropic chemical shifts of carbon atoms C(1) and C(2) are 24.3 and 43.8 ppm, respectively. Upon formation of the disclosed compound, these two peaks shifted to the downfield direction and now appear at 38.0 and 49.4 ppm. The observation that the carbon atom C(1) exhibits a significantly larger shift is indicative of the copper ion bound to the sulfur atom. The facts that the observed shifts of the ligand precursor are small (less than 15 ppm) upon coordination and that no spinning side bands were observed at the relatively low spinning speed used for the crystals of the invention suggest that the Cu ion is a diamagnetic species (i.e. Cu+). If the Cu oxidation state were 2+, much larger shifts would be observed due to the paramagnetic contribution to the isotropic shift, especially for the carbon atom C(1). Furthermore, a large number of spinning sidebands arising from the large paramagnetic shift anisotropy (PSA) are expected, which are often observed for the carbon atoms near a paramagnetic center. For example, in a Cu2+-containing metal-organic framework, HKUST-1, the resonance of the carboxylate carbon in the benzenetricarboxylate ligand exhibits a very large upfield paramagnetic shift of 256.8 ppm from 170.8 ppm of the free ligand (benzenetricarboxylic acid) to −86 ppm of HKUST-1. The aromatic carbons, on the other hand, experience paramagnetic shifts of 98-92 ppm, but to the opposite direction (i.e., the shift is downfield) [1, 2]. In addition, at 10 kHz (a spinning speed comparable to that used in this study) a larger number of intense sidebands were seen resulting from the PSA. Therefore, the NMR data are consistent with single-crystal XRD results that the oxidation state of copper in the crystals of the invention is +1, rather than +2.

Figure 20:
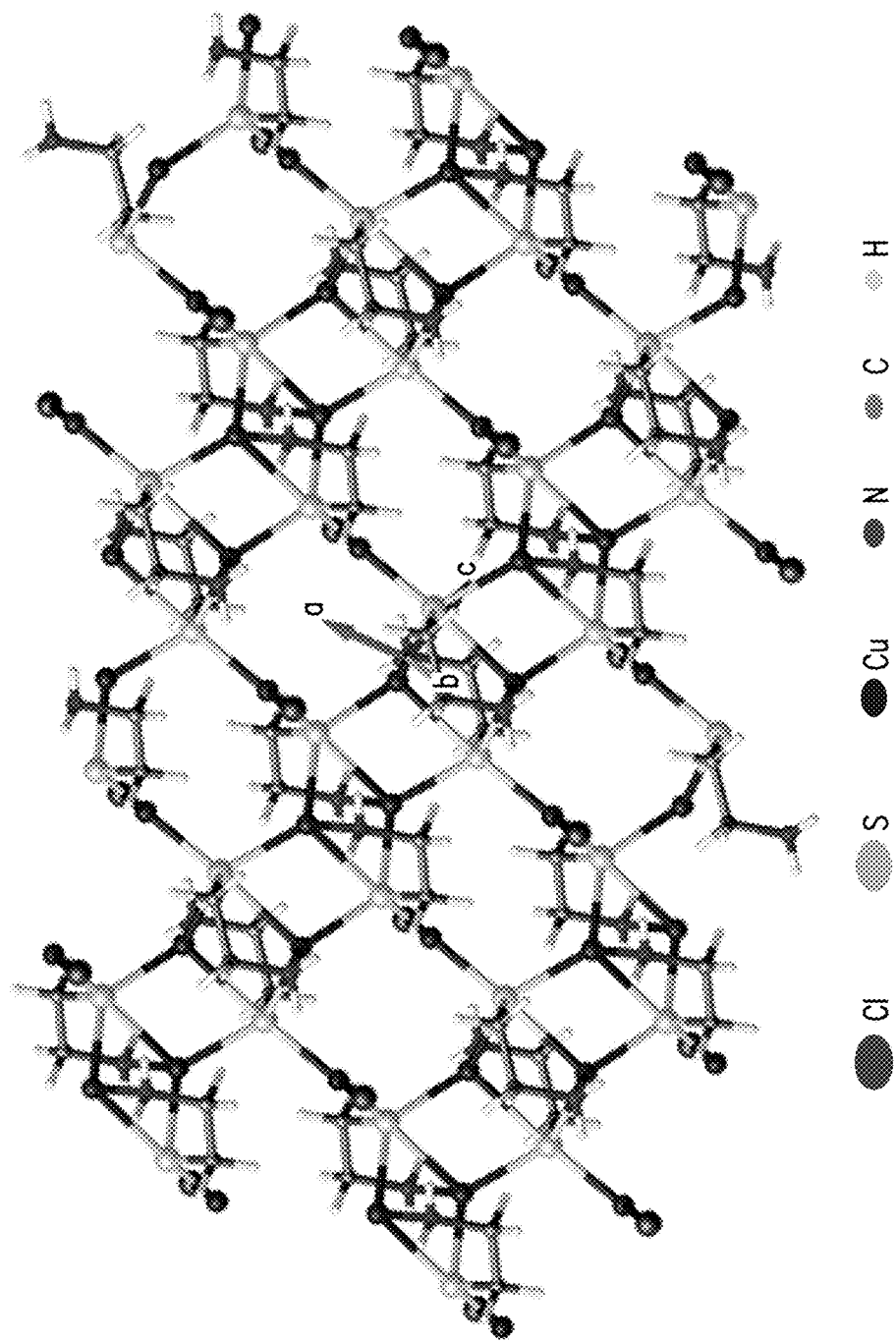
FIG. 20 depicts the structure of a particular crystalline form of the disclosed complex. Selected distances and angles are Cu(1)-S(1) 2.3167(9) Å; Cu(2)-S(1), 2.2474(8) Å; Cu(2)-Cl(1), 2.2739(12) Å.

The copper-complex material of the invention has less atoms in its repeating unit cell than the previous reported Cu-Cy crystals $Cu_{13}Cl_{13}(SR')_6$ and $Cu_8Cl_8(SR')_6$, where $R'=CH_2CH_2NH_3$. The structure of the disclosed copper-complexes is simpler. As seen in FIG. 20, both ends (thiol group and amine group) from SR bond to Cu(1), the thiol group forms a covalence bond with Cu(1) while the electron pair from amine group forms coordinate bond with the same atom. While in the previous Cu-Cy structures, only thiol groups bond with Cu atoms. Here, chelation may be responsible for stabilizing the structure.

Figure 4:
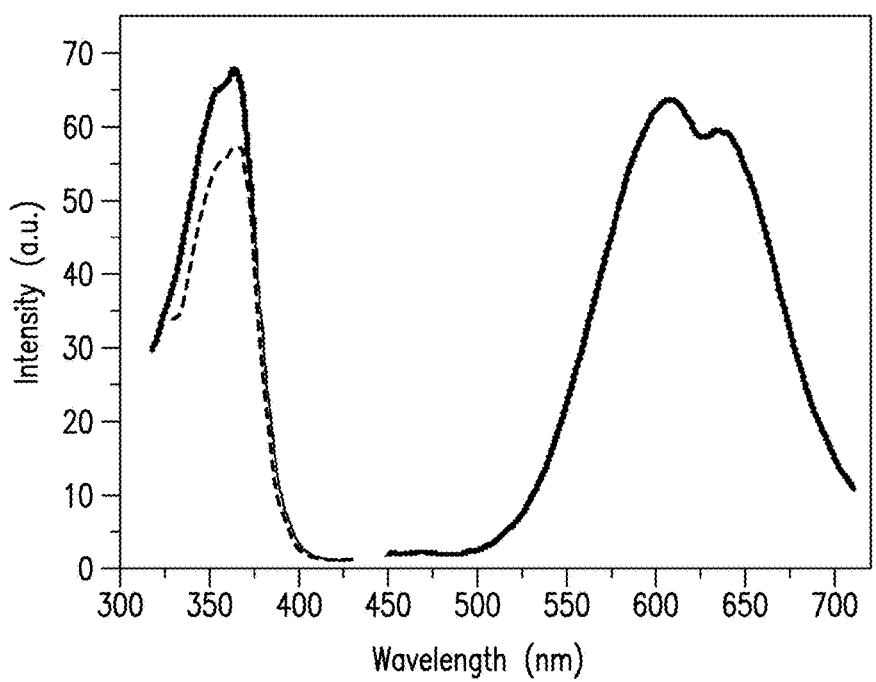
FIG. 4 depicts the photoluminescence emission spectra on the right of Cu-Cy crystals after excitation at 360 nm. Excitation spectra are shown on the left. The 607 nm emission has the solid line excitation and the 633 nm emission has the excitation spectrum represented by the dashed line.

The disclosed Cu-Cy emits visible light when excited by ultra violet or X-ray electromagnetic radiation, i.e., photoluminescence and X-ray luminescence. This luminescence is observed over a pH range of from about 5 to about 14. FIG. 4 shows the photoluminescence emission and excitation spectra of the disclosed Cu-Cy crystals in water. Two red emissions peaking at 607 nm and 633 nm are observed from the Cu-Cy crystals in water, which indicates two luminescence emitting centers.

Figure 5:
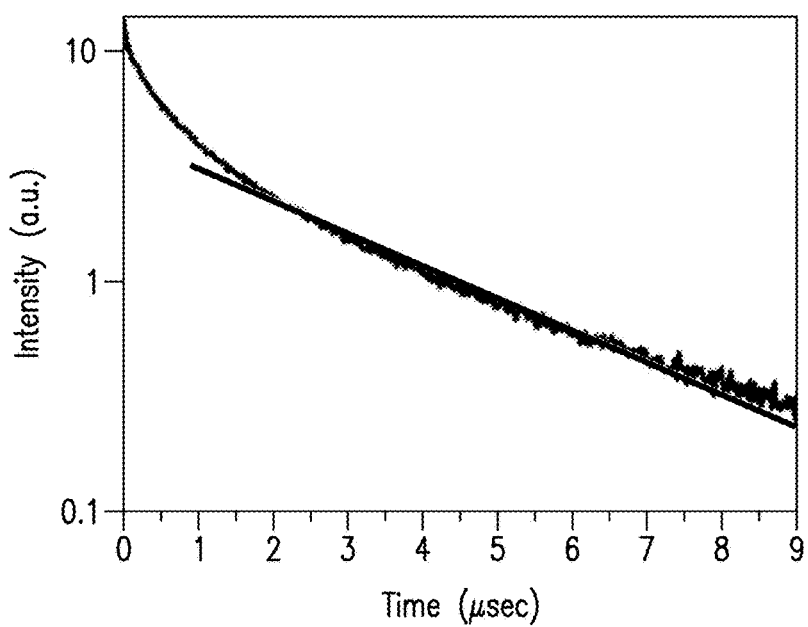
FIG. 5 depicts the lifetime spectrum of Cu-Cy crystals. A straight line is plotted as a comparison to show that the close linear property of the decay curve portion after 2 µs.
Figure 6:
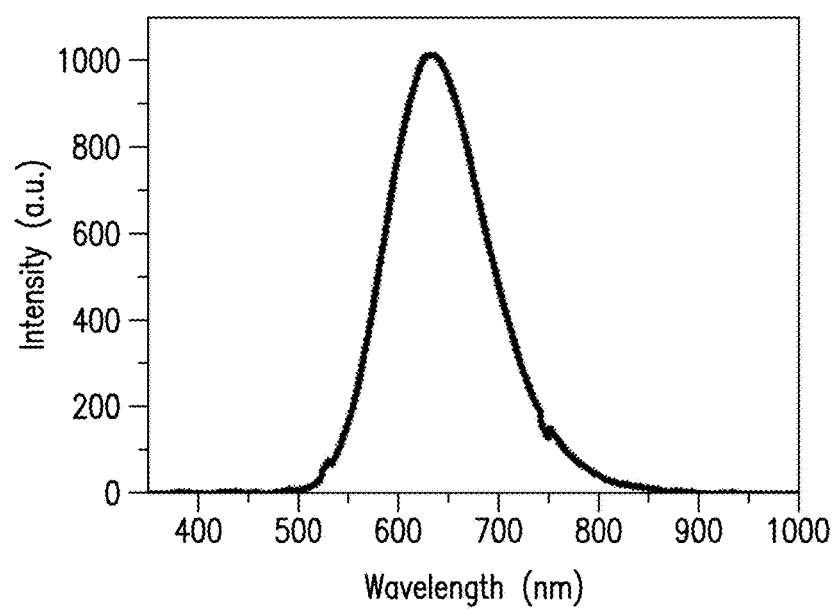
FIG. 6 depicts the X-ray luminescence spectrum of the Cu-Cy crystals of the invention.

The lifetime spectrum of Cu-Cy particles was plotted in a log(intensity)—time format as shown in FIG. 5. The decay curve show a non-linear property in the logarithmic scale plot (especially the portion before 2 μs), which means that the intensity is not decaying in time by a simple exponential function. The disclosed Cu-Cy crystals exhibit intensive luminescence centered at 633 nm when they are excited by X-rays (FIG. 6).

Figure 7:
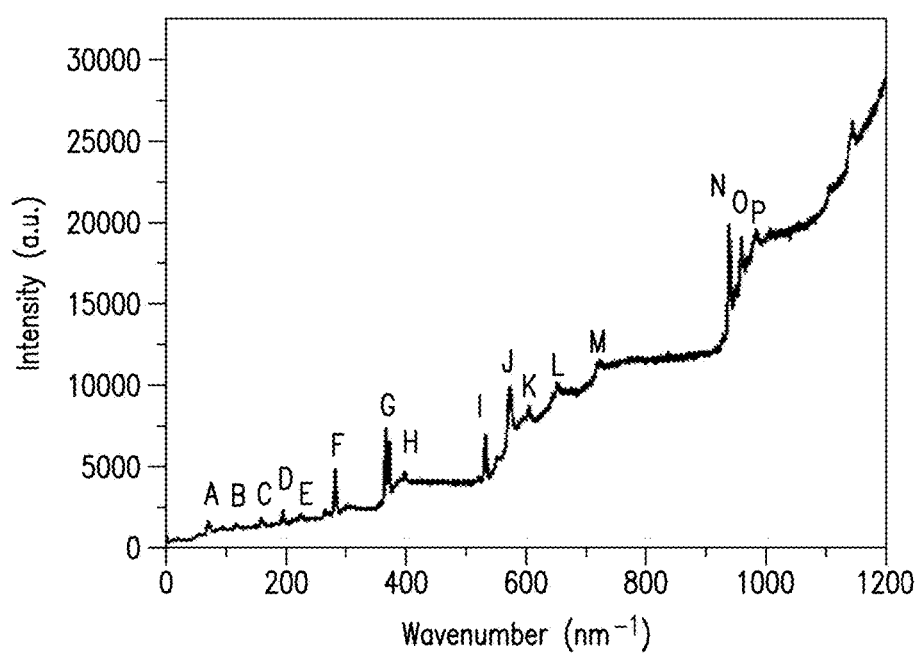
FIG. 7 depicts the XPS profile of Cu-Cy crystals of the invention. The peaks are assigned as follows—peak A Cu(3p), peak B Cu(3s), peak C S(2p), peak D Cl(2p), peak E S(2p), peak F Cl(1s), peak G Ag(3d), peak H N(1s), peak I O(1s), peak J Ag(3p3/2), peak K Ag(3p1/2), peak L Cu(Auger), peak M Ag(3s), peak N Cu(2p3/2), peak O Cu(2p1/2) and peak P O(Auger).
Figure 8:
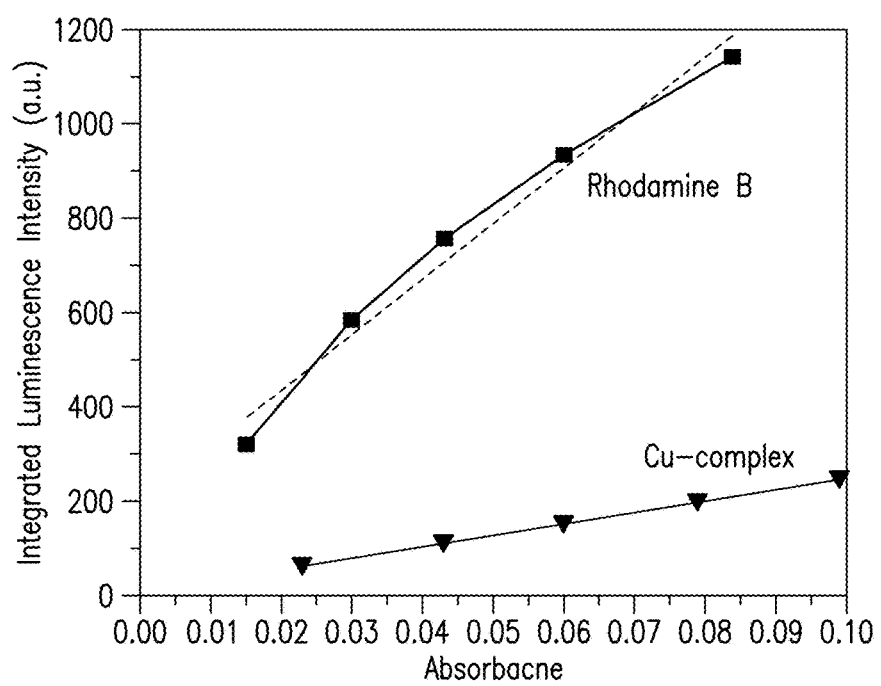
FIG. 8 depicts Quantum yield measurement of the disclosed Cu-Cy crystals in water by using Rhodamine B as a standard (■). The straight line is the linear fitting for Rhodamine B while the linear fitting for the Cu-Cy in water is almost entirely coincidental with the depicted values (▼).
Figure 22:
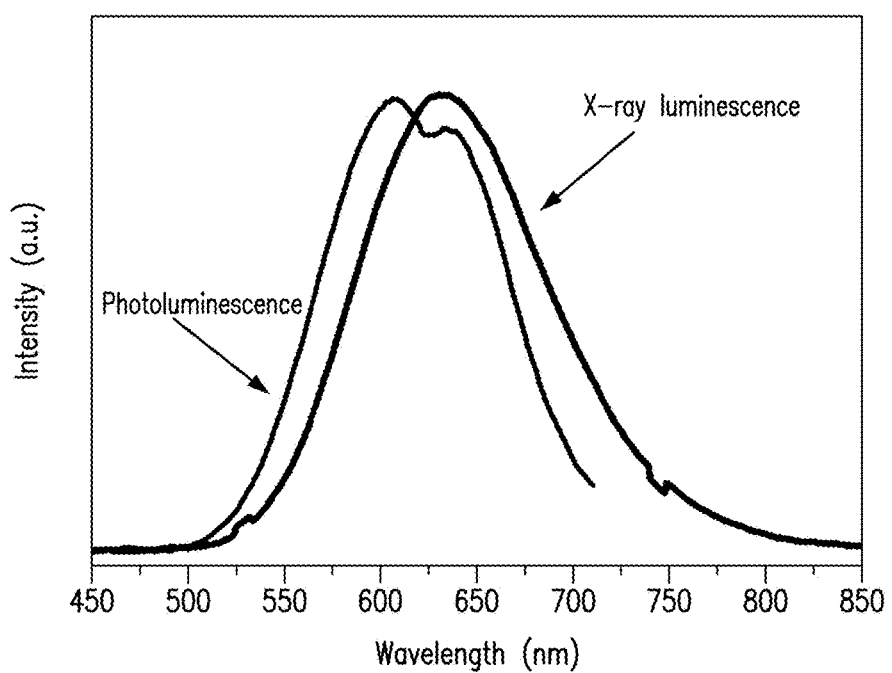
FIG. 22 depicts photoluminescence emission spectrum (black, $\lambda_{ex}$=360 nm) and X-ray luminescence of Cu-Cy.
Figure 23:
FIGS. 23A-D show a comparison of X-ray (2Gy) destruction of MCF-7 cells using Cu-Cy particles of the invention. The images show MCF-7 live (green, calcein-AM stain) and dead (red, EthD-1 stain) cells. The scale bar is 100 µm.

FIG. 22 depicts the photoluminescence emission spectrum (360 nm) and X-ray luminescence of Cu-Cy together. The XPS profile of Cu-Cy crystals of the invention is shown in FIG. 7. Without wishing to be limited by theory the labeled peaks are assigned as follows: peak A Cu(3p), peak B Cu(3s), peak C S(2p), peak D Cl(2p), peak E S(2p), peak F Cl(1s), peak G Ag(3d), peak H N(1s), peak I O(1s), peak J Ag(3p3/2), peak K Ag(3p1/2), peak L Cu(Auger), peak M Ag(3s), peak N Cu(2p3/2), peak O Cu(2p1/2) and peak P O(Auger). Ag signals are seen because Ag film is used for coating on the surface of a small silicon wafer in XPS sample preparation. O signals displayed in the XPS are due to absorbance by O on the sample surface.

Methods

Photodynamic Therapy

Disclosed herein are methods for using the disclosed complex as a treatment for cancer. The methods and uses relate to the ability of the disclosed Cu-Cy complex to serve as an effective agent for photodynamic therapy. Photodynamic therapy (PDT) has attracted ever-growing attention as a promising modality in the treatment of cancer. However, due to the poor tissue penetration by light, PDT has rarely been applied for deep-seated tumors. This problem can be solved if photosensitizers are activated by X-rays, which are able to penetrate deeply into tissues. Previous attempts at using X-rays to activate photosensitizers were not very successful, since the traditional PDT photosensitizers cannot efficiently be activated with X-rays. Photodynamic therapy (PDT) and photothermal therapy (PTT) are two major cancer treatments by using electromagnetic radiation. Cells are killed by singlet oxygen generated in PDT while high temperature is utilized in PTT.

Accordingly, the disclosed Cu-Cy complex can be used to treat a variety of mammalian tumors. As used herein, the term "treating" refers to: (i) preventing a disease, disorder or condition from occurring in a mammal, animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition. For example, with respect to cancer, treatment may be measured quantitatively or qualitatively to determine the presence/absence of the disease, or its progression or regression using, for example, reduction in tumor size, a reduction in the rate of metastasis, and/or a slowing of tumor growth, and/or no worsening in disease over a specified period of time or other symptoms associated with the disease or clinical indications associated with the pathology of the cancer.

As mentioned above, the disclosed Cu-Cy complex and methods can be used in imaging of target tissue or tumors, to treat any number of cancers or tumors or both. The disclosed Cu-Cy complex is particularly suited for the imaging and/or treatment of deep tissue tumors, such breast cancer, ovarian cancer, brain cancer, lung cancer, hepatic cancers, and the like. Types of mammalian tumors that can be treated using the disclosed Cu-Cy complex and methods include, but are not limited to all solid tumors, cutaneous tumors, melanoma, malignant melanoma, renal cell carcinoma, colorectal carcinoma, colon cancer, hepatic metastases of advanced colorectal carcinoma, lymphomas (including glandular lymphoma), malignant lymphoma, Kaposi's sarcoma, prostate cancer, kidney cancer, ovarian cancer, lung cancer, head and neck cancer, pancreatic cancer, mesenteric cancer, gastric cancer, rectal cancer, stomach cancer, bladder cancer, leukemia (including hairy cell leukemia and chronic myelogenous leukemia), breast cancer, solid breast tumor growth, non-melanoma skin cancer (including squamous cell carcinoma and basal cell carcinoma), hemangioma multiple myeloma, and glioma. In one embodiment, the cancer is brain, breast, lung, pancreatic, hepatic, colon, melanoma, ovarian cancer, or metastases thereof. In addition, embodiments for the invention can be adapted for non-solid tumors, including leukemias or lymphomas, via whole-body PDT therapy using the disclosed Cu-Cy complex.

In one aspect, the methods include administering systemically or locally the disclosed Cu-Cy complex. Any suitable route of administration may be used, including, for example, topical, intravenous, oral, subcutaneous, local (e.g. in the eye) or by use of an implant. Advantageously, the small size, colloidal stability, non-agglomeration properties, and enhanced half-life of the disclosed Cu-Cy complex makes it especially suitable for intravenous administration. Additional routes of administration are subcutaneous, intramuscular, or intraperitoneal injections in conventional or convenient forms. For topical administration, the disclosed Cu-Cy complex can be in standard topical formulations and compositions including lotions, suspensions or pastes. For example, ICG encapsulation of the disclosed Cu-Cy complex can be administered by various means, but preferably by intravenous injection.

The dose of photosensitizer-encapsulated nanoparticles may be optimized by the skilled person depending on factors such as, but not limited to, the photosensitizer chosen, the nature of the therapeutic protocol, the individual subject, and the judgment of the skilled practitioner. Preferred amounts of photosensitizer-encapsulated nanoparticles are those which are clinically or therapeutically effective in the treatment method being used. Such amounts are referred herein as "effective amounts".

Depending on the needs of the subject and the constraints of the treatment method being used, smaller or larger doses of disclosed Cu-Cy complex may be needed. The doses may be a single administration or include multiple dosages over time.

The disclosed Cu-Cy complex is administered to the subject and the tumor or tissue in the subject is exposed for a sufficient amount of time to a photo-activating amount of light at a wavelength that activates the disclosed Cu-Cy complex sufficient to obtain the desired response. In some cases, the desired response is the ability to bioimage or detect the target tissue or tumor, or to perform photodynamic therapy using the methods and disclosed Cu-Cy complex for a sufficient period of time effective to inhibit or reduce tumor growth or tumor size. The desired response may be compared to a control if desired.

In general, disclosed are methods for treating tumors or imaging targeted tissue in a subject, comprising:
a) administering to a subject an effective amount of a compound having the formula:

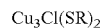

wherein R is —CH$_2$CH$_2$NH$_2$ (the disclosed Cu-Cy complex); and
b) exposing the tumor or targeted tissue to a photo-activating amount of electromagnetic radiation at a wavelength that actives the compound.

In one aspect the electromagnetic radiation can be from a source of X-rays or from a source of ultraviolet light. The tumor or targeted tissue is typically irradiated for a sufficient amount of time to obtain a desired response. The formulator, however, can use any source of radiation, for example, a radiation source chosen from an X-ray source, a gamma-ray source, a beta-ray source, a source of proton emission, a source of electron emission, or a source of neutron emission The desired response is determined by the formulator or user.

In one aspect, disclosed is a method for treating cancer, comprising:
a) contacting a cancerous cell with an effective amount of the disclosed Cu-Cy complex; and
b) irradiating the Cu-Cy complex.

In another aspect, the disclosed method comprises:
a) contacting a tumor with an effective amount of the disclosed Cu-Cy complex; and
b) irradiating the Cu-Cy with a source of X-rays to produce single oxygen.

The treatment can be performed in any manner chosen by the formulator. For example, the complex can be injected via syringe or any other suitable delivery means to the site of the tumor. The source of radiation can be applied by any convenient means compatible with the location of the tumor. The method can be conducted during surgery, for example, with or without excising the tumor. In one iteration of this aspect, the complex can be administered topically to cancers of the skin.

Another aspect of the disclosure relates to a method for treating cancer in a subject, comprising:
a) co-administering to the cancer cells compound having the formula:

wherein R is —CH$_2$CH$_2$NH$_2$ and a radio isotope; and
b) optionally irradiating the cancer cells with a source of electromagnetic radiation.

In one embodiment of the disclosure the metastable isotope of technetium, Tc-99 m, is co-administered with the Cu-Cy. The admixture of Cu-Cy and the radio isotope can be further irradiated. The further irradiation can be accomplished using a source of radiation is chosen from an X-ray source, a gamma-ray source, a beta-ray source, a source of proton emission, a source of electron emission, or a source of neutron emission.

Another aspect relates to the use of the disclosed Cu-Cy complex for making a medicament for the treatment of cancer. In still another aspect, disclosed herein is the use of the disclosed Cu-Cy complex as a treatment for cancer.

Without wishing to be limited by theory, particles of the disclosed Cu-Cy complex can be efficiently activated by X-rays to produce singlet oxygen, i.e., as a means from providing photodynamic therapy (PDT). PDT uses several different mechanisms to destroy tumors. A photosensitizer can target tumor cells directly, inducing necrosis or apoptosis. Alternatively, by the targeting of tumor vasculature, the tumor can be starved of oxygen-carrying blood.

As it relates to the use of the disclosed Cu-Cy complex for cancer treatment, the Cu-Cy photosensitizers have several unique characteristics:
(i) Cu-Cy particles themselves are photosensitizers that can be activated directly by X-rays. As such, there is no need to use other sensitizing agents or nanoparticles;
(ii) Cu-Cy particles emit luminescence, permitting their use as a diagnostic imaging agent;
(iii) Cu-Cy particles can be fabricated at the nanoscale to increase water solubility and cellular uptake;
(iv) Cu-Cy complex in the form of nanoparticles can also be tagged with functional groups for targeted delivery;
(v) Cu-Cy complex have low cytotoxicity; and
(vi) Cu-Cy complex are easy to synthesize and inexpensive.

The disclosed Cu-Cy particles can be used for deep-seated cancers, thereby surpassing the limits of traditional PDT which is presently restricted to treatment of superficial tumors.

The X-ray induced Cu-Cy photosensitizer provides a novel concept for PDT. In addition, Cu-Cy particles can be used for cell imaging during cancer treatment because these particles have strong photoluminescence and X-ray excited luminescence. Overall, the Cu-Cy photosensitizers of the invention will have a significant impact on the treatment of deep cancer.

Figure 9:
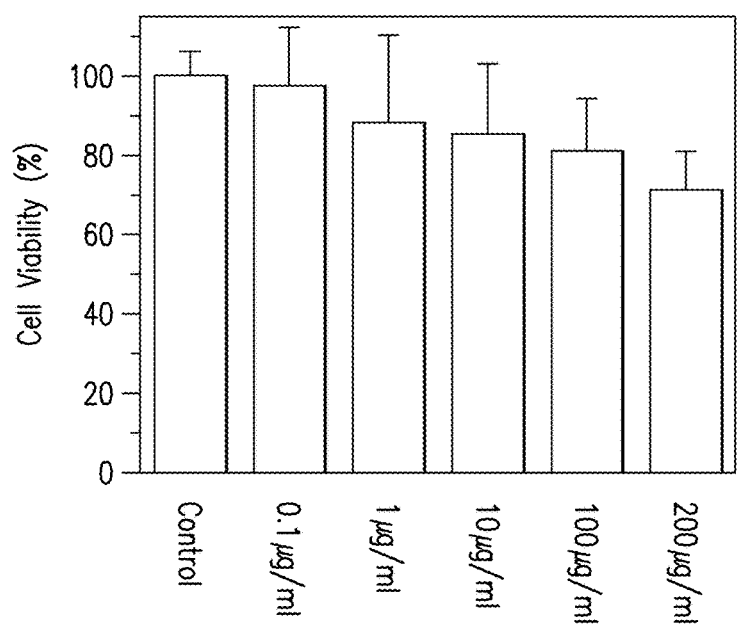
FIG. 9 depicts the viabilities of MCF-7 cells at different concentrations of the disclosed Cu-Cy crystals.

The toxicity of Cu-Cy crystals in MCF-7 cells was evaluated using an MTT (3-(4,5-dimethylthiazol-2-yl)-2,5-diphenyltetrazoliumbromide) assay. 2 mg of the Cu-Cy crystals were well ground and sonicated before being dissolved in 1 mL of DI water (control) for the measurement. As seen in FIG. 9, the cellular viability gradually decreased from about 95% to about 70% when the Cu-Cy concentration was increased from 0.1 µg/ml to 200 µg/ml.

Figure 10A:
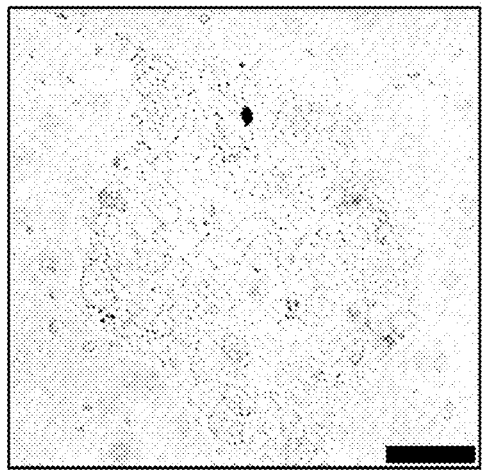
FIGS. 10A-10D depict the images of MCF-7 cells incubated for 24 hours with the disclosed Cu-Cy crystals. The cells were stained with 4',6-diamidino-2-phenylindole (DAPI).
Figure 10B:
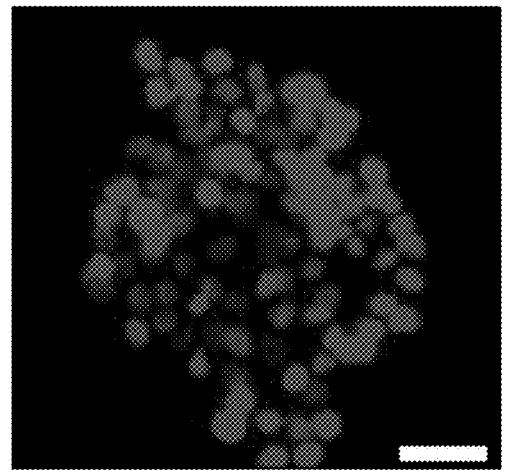
Figure 10C:
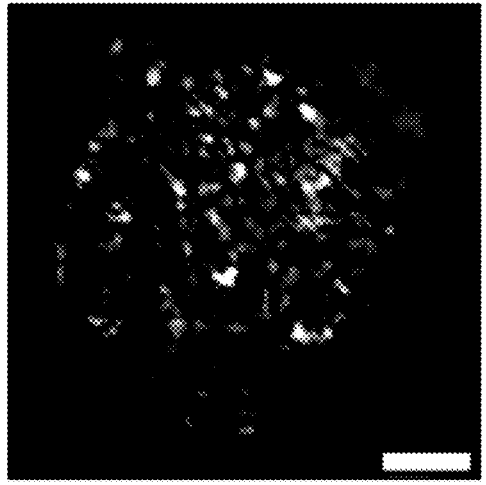
Figure 10D:
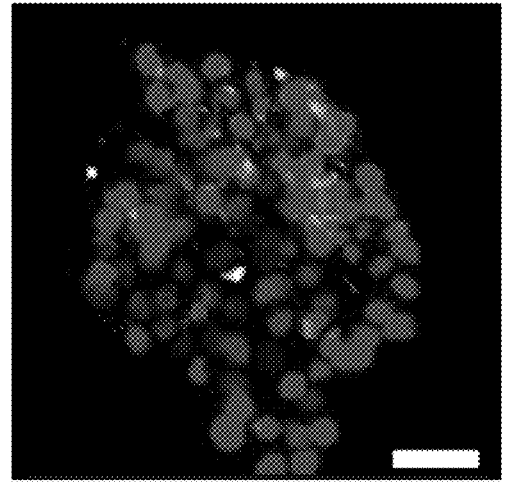

FIG. 10A is the bright-field image of MCR-7 breast cancer cells after incubation with the disclosed Cu-Cy complex. In order to review the cell uptake of the Cu-Cy crystals, we incubated the crystals with human breast cancer (MCF-7) cells for 24 hours. Cells were then stained with 4',6-Diamidino-2-phenylindole (DAPI) and their nuclei were clearly seen when using excitation of 405 nm and filtering red wavelengths out (FIG. 10B). The red emission shown in FIG. 10C results from Cu-Cy crystals excited at 360 nm. FIG. 10D is a photo combination of FIGS. 10B and 10C.

Human Hepatocellular Liver Cells

FIGS. 11A-11D depict the effectiveness of the Cu-Cy material as causing cell death when irradiated with UV light or X-ray. For example, in FIGS. 11A-11D, the fluorescence images of human hepatocellular liver cells were taken before and after the UV light exposure (350 nm, for 2 minutes, from an OLYMPUS IX71 microscope). Calcein and Ethidium homodimer 1 (EthD-1) were used as the stains showing cell alive (green) and death (red) respectively.

Each of the images was taken right after the staining without further liver cell incubation. As seen in FIGS. 11A-11B, UV light alone is ineffective in causing cell death. The presence of Cu-Cy crystals alone (FIG. 11C) does not result in significant cell death; however, when irradiated with a UV source, there is significant cell death as demonstrated in FIG. 11D.

MCF-7 Breast Cancer Cells

Photo-induced toxicity was then applied to cancer cells. FIGS. 12A-12D displays a similar fluorescence imaging study but using breast cancer (MCF-7) cells. As in the case of the cancer cells, significant cellular death occurs when cells exposed to the disclosed Cu-Cy complex are irradiated with a source of UV light.

As stated herein above, the disclosed Cu-Cy compound also absorbs X-rays and emits a luminescent spectrum. FIG. 13A-13D depicts the MCF-7 cell viabilities by fluorescence images with and without Cu-Cy crystals and with and without X-ray irradiation. As with UV radiation, X-ray irradiation of cells incubated with the disclosed Cu-Cy complex is also an effective method for causing cell death.

FIGS. 14A-D depict fluorescence images of MCF-7 cells before and after 1 Gy X-ray exposure by an OLYMPUS IX71 microscope. Calcein and ethidiumhomodimer 1 (EthD-1) were used as the stains showing cells alive (green) and dead (red) respectively. Each of the images was taken immediately after staining, without further cell incubation. As indicated, applied X-ray dose alone does not kill the cells without Cu-Cy particles (FIG. 13A and FIG. 13B). There is little cell death in the presence of Cu-Cy particles alone (FIG. 13C). When the Cu-Cy and X-ray treatment are coupled, significant cell destruction results (FIG. 13D).

Human Prostate Cancer (PC-3) Cells

FIG. 14A-14D show comparable results for human prostate cancer cells incubated with the disclosed Cu-Cy compound and irradiated with an X-ray source versus control. As such, the combination of the disclosed Cu-Cy material and a source of radiation provides an effective method for inducing cell death.

Figure 15:
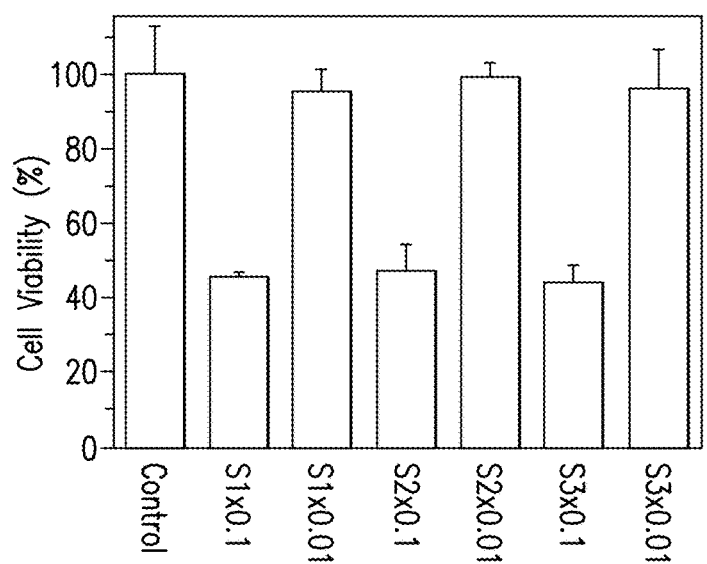
FIG. 15 depicts the cell (PC-3) viabilities in the presence of (a) Cu-Cy crystals, (b) UV light treated Cu-Cy crystals, and (c) X-ray treated Cu-Cy crystals at two concentrations respectively.
Figure 16:
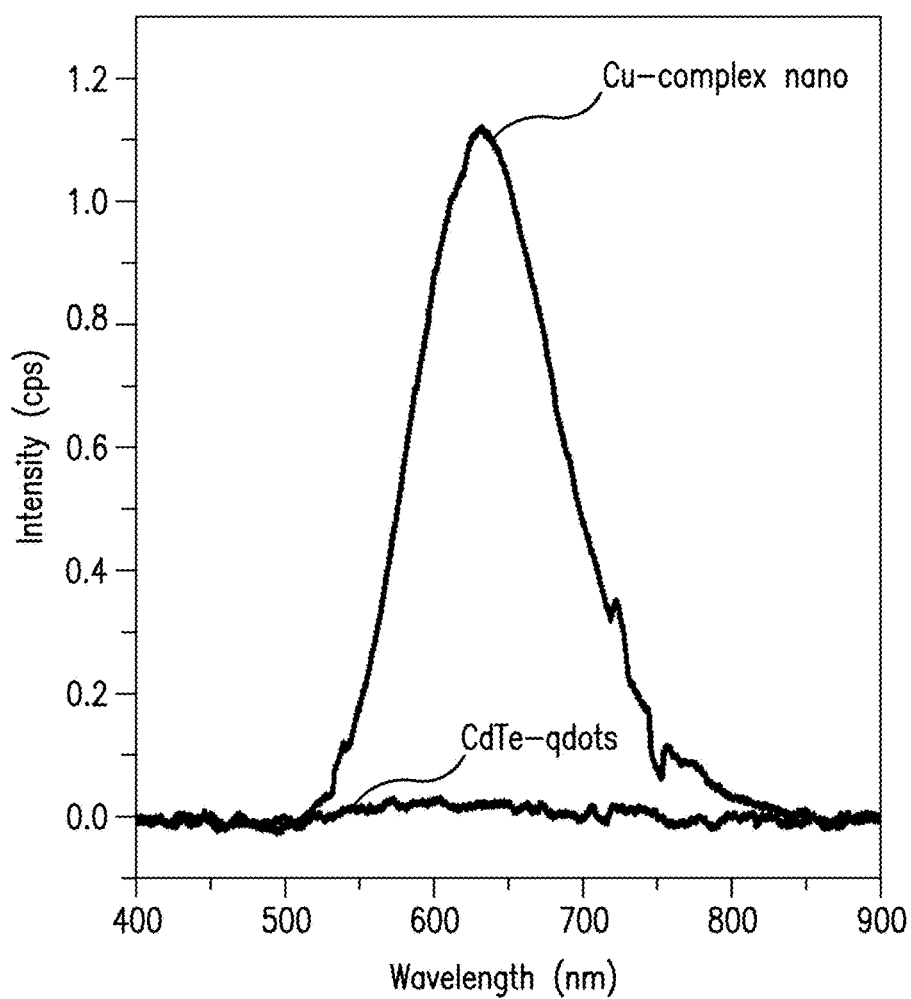
FIG. 16 depicts X-ray luminescence of disclosed Cu-Cy invention versus CdTe quantum dots. Both measurements are taken in water at a concentration of 0.02M.
Figure 17:
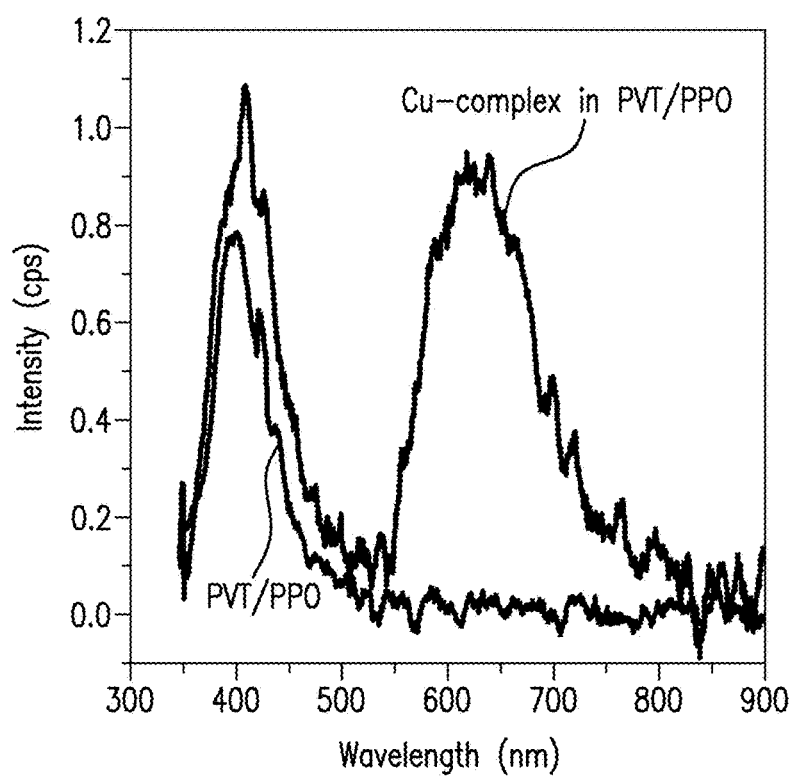
FIG. 17 depicts X-ray luminescence of polyvinyl toluene/ 2,5-diphenyloxazole (PVT/PPO) polymer and Cu-Cy/PVT/ PPO composites. The volume of Cu-Cy in PVT is only 1%.

The cellular toxicity in PC-3 cells at various concentrations of Cu-Cy (S1), Cu-Cy treated by UV light (S2), and Cu-Cy treated by X-ray irradiation (S3) is depicted in FIG. 15. Reading FIG. 15 from left to right: Control sample, PC-3 cells incubated with 0.2 mg/mL S1, PC-3 cells incubated with 0.02 mg/mL S1, PC-3 cells incubated with 0.2 mg/mL S2, PC-3 cells incubated with 0.02 mg/mL S2, PC-3 cells incubated with 0.2 mg/mL S3, and PC-3 cells incubated with 0.02 mg/mL S3.

Singlet Oxygen

Figure 18A:
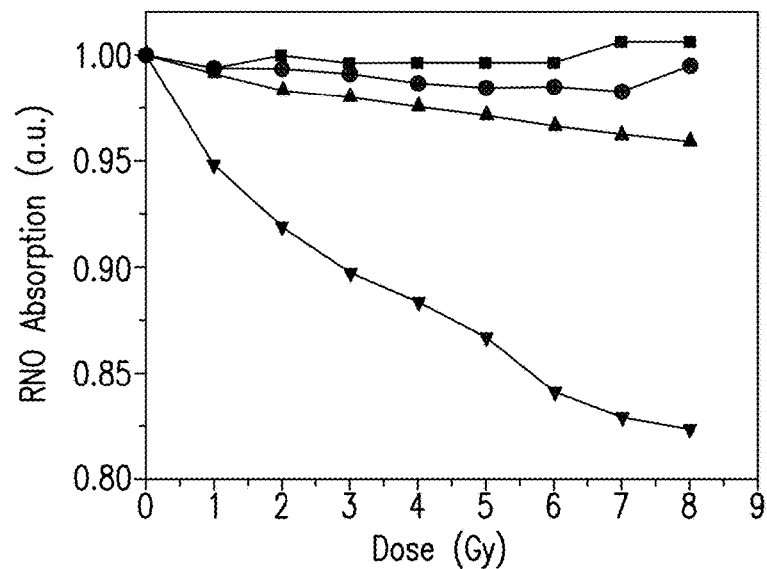
FIGS. 18A & 18B depicts singlet oxygen production in PPIX (▲), ZnO (●), and the disclosed Cu-Cy (▼) versus control (■) when excited by X-rays (FIG. 18A); and singlet oxygen production in PPIX (●) and Cu-Cy (▲) versus control (■) using UV light (365 nm) (FIG. 18B).
Figure 18B:
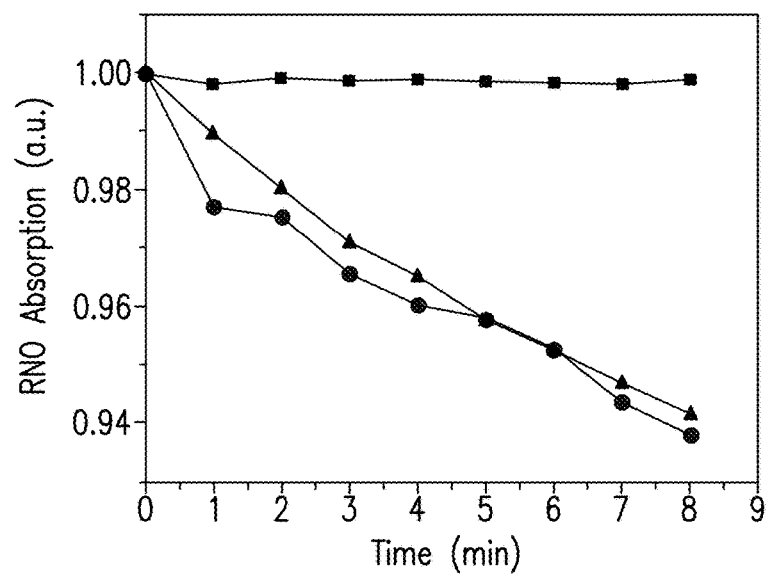

To evaluate whether Cu-Cy particles produce singlet oxygen as a method for treating cancer via irradiation by X-rays the p-nitrosodimethylaniline (RNO)-imidazole(ID) method (Kraljić et al., "A New Method for the Detection of Singlet Oxygen in Aqueous Solutions," *Photochemistry and Photobiology*, Vol. 28: Issue 4-5, 577-581 (1978)) was used to detect whether singlet oxygen was produce using various X-ray doses. RNO is a water-soluble molecule with absorption that can be quenched irreversibly by singlet oxygen in the presence of ID. FIG. 18A depicts the decrease in RNO absorbance over a range of X-Ray doses for zinc oxide, protoporphyrin IX (PPIX) and the disclosed Cu-Cy complex versus control. The amount of singlet oxygen formation by ZnO as measured by the loss in RNO absorption was relatively low as compared with control. PPIX exhibited a modest increase over ZnO. The disclosed Cu-Cy complex exhibited an almost linear relationship of increasing singlet oxygen formation and was six-times greater than PPIX at 8 Gy. FIG. 18B depicts the same experiment omitting ZnO, but using ultra violet light as the radiation source.

Singlet oxygen measurement.

p-nitrosodimethylaniline(RNO) (0.225 mg) and imidazole(ID) (16.34 mg) were added to 30 mL DI water, which was air saturated by sufficient air bobbling. The sample solution was prepared by adding 1 mg of testing sample (Cu-Cy, PPIX, or ZnO) into 3 mL above RNO-ID solution. Then, the RNO-ID solution and sample solutions were exposed under different X-ray doses (0 to 8 Gy) using a Faxitron RX-650 cabinet X-ray system (Faxitron X-ray LLC, USA). Meanwhile, the intensity of RNO absorption peak at 440 nm of different solutions was monitored by a Shimadzu UV-vis spectrophotometer.

Subcutaneous Tumor Model

Figure 24:
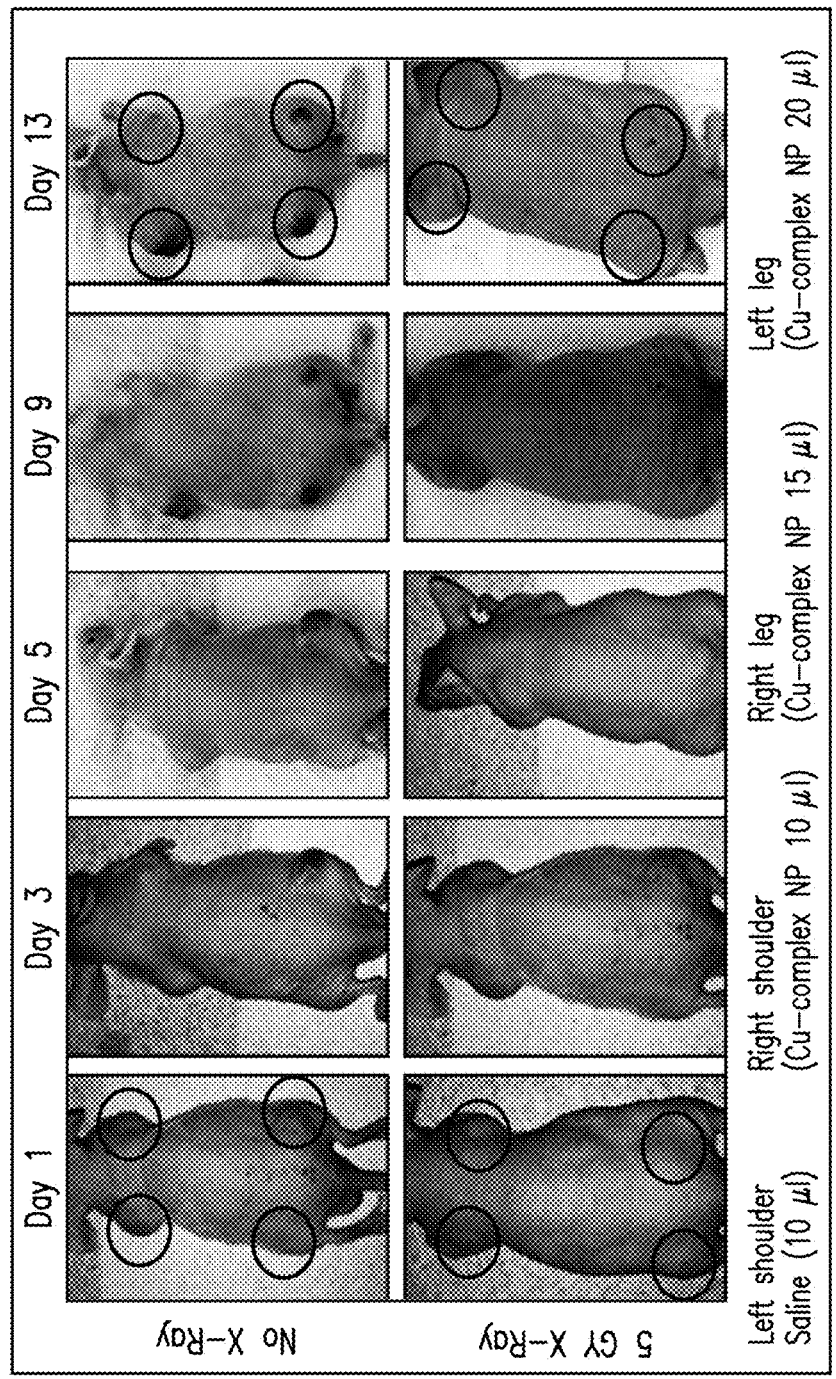
FIG. 24 shows time-dependent in vivo images of mice with different sized MCF-7 tumors after treatment at 1, 3, 5, 9 and 13 days.
Figure 25:
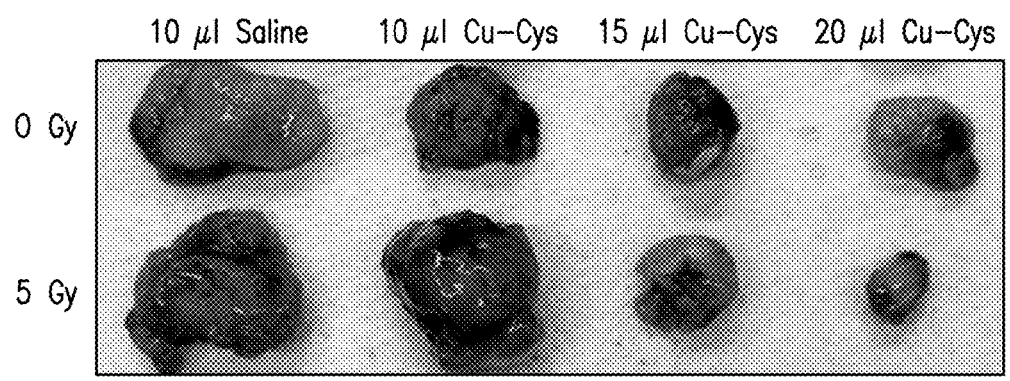
FIG. 25 pictures the breast tumors collected after MCF-7 tumor-bearing mice were sacrificed on day 13 of treatment.

A suspension of $10 \times 10^6$ MCF-7 cancer cell lines was injected subcutaneously into flanks on both shoulder and leg area of nude mice. Mice were monitored on a daily basis for the growth of tumors (FIG. 24). When the tumors reached about 3-4 mm in diameter, mice were divided randomly into two groups: one group received X-ray irradiation and the other group did not. Saline (10 μL, as control, left shoulder) and Cu-Cy with concentration about 0.8 mg/mL (10 μL-right shoulder, 15 μL-left leg and 20 μL-right leg) were injected intra-tumorally. At one minute post-injection, mice were anesthetized with 2% (v/v) isofluorane, and tumors were irradiated with an X-ray dose of 5 Gy. Without X-ray treatment (top row), the tumors grew as time progressed, and there was no apparent size difference among Cu-Cy dosages of 10, 15, and 20 μl. Meanwhile, the tumors with no Cu-Cy (saline only) treatment were larger than the tumors with Cu-Cy treatment. This observation suggests that the Cu-Cy exhibits slight toxicity in vivo, but does not significantly reduce tumor size or growth, regardless of the applied Cu-Cy dose. However, with X-ray radiation (bottom row), the tumor growth was greatly reduced for 15 and 20 μL Cu-Cy dosages. The animals were sacrificed via $CO_2$ inhalation and cervical decapitation on the day 13 of tumor growth. The tumors were surgically dissected and are shown in FIG. 25. Absent X-ray radiation (top row), the tumors without Cu-Cy treatment grew to a somewhat larger volume than those treated by Cu-Cy, which indicates the minor toxicity from the Cu-Cy particles themselves. The similar size of tumors treated by 10, 15, or 20 μL of Cu-Cy reveals that high Cu-Cy dosage does not affect tumor growth. However, when activated by X-ray, the higher Cu-Cy dosage greatly reduced the tumor volume (bottom row). X-ray radiation in the absence of Cu-Cy did not contribute to any tumor size reduction. This is seen by comparing the two tumors treated with saline with and without X-ray radiation. For the treatment with 20 μL of Cu-Cy particles at 5 Gy dose, the tumor size is reduced to about 3 mm in diameter while the untreated tumor size is about 10 mm in diameter. These observations and conclusions are consistent with the work shown in FIG. 24. The preliminary results show that Cu-Cy is a promising photosensitizer for cancer treatment.

Cell Culture and Cell Uptake of Cu-Cy Particles

The MCF-7 cell lines were purchased from ATCC (American Type Culture Collection) and grown in chamber slides in RPMI 1640 and Ham's F12K medium, respectively, supplemented with 100 units/mL aqueous penicillin G, 100 μg/mL streptomycin, and 10% fetal bovine serum at concentrations that allowed 70% confluence in 24 h. On the day of experimentation, cells were washed with pre-warmed PBS and incubated with pre-warmed phenol-red-reduced OptiMEM media for 30 min. before the addition of 50 μg of Cu-Cy particles. Cells were incubated with Cu-Cy for 24 hours at 37° C., then washed with PBS three times, fixed with 4% paraformaldehyde, counterstained with 4',6-diamidino-2-phenylindole and Alexa-Flour Phalloidin, mounted, and visualized by a fluorescence microscope.

Cytotoxicity Test

Cytotoxicity was evaluated using the MTT assay. Approximately 2,000 cells/well MCF-7 cells were seeded into 96-well plates and allowed to grow for 48 hours in an incubator (Sanyo, Japan, 5% CO2, 37° C., humidified atmosphere). On the day of the experiment, after removing the culture medium, different volumes of media containing Cu-Cy particles were added to their respective wells and cytotoxicity was evaluated after 24 h of cell incubation In Vitro Cell Destruction Using Fluorescence Imaging MCF-7 cells were seeded into two 6-well plates (A and B) at 5,000 cells/well and incubated for 48 h at 37° C. in a humidified atmosphere of 5% v/v $CO_2$ at dark. On the day of the experiment, the culture medium was removed and 5 mL medium containing 0 and 40 μg/ml Cu-Cy particles were added to different wells. After other 24 hours cell culture, the cells in plate A were irradiated with 2 Gy X-ray and cells in plate B were not. Then, cells were incubated with 500 μL of dye mixture (Calcein and EthD-1) for 30 min under standard cell culture conditions in the dark. Unincorporated dyes were removed by washing, following which culture wells were replenished with media. The cells were viewed under an OLYMPUS IX71 fluorescence microscope.

Radiation Detection

Further disclosed herein is the use of the disclosed Cu-Cy complex for the detection of radiation. The radiation can be from any source, inter alia, alfa, gamma, beta, neutron, cosmic rays or any high energy particles. In addition, the disclosed complex can be used for medical imaging such as an X-ray intensifier, detectors for computed tomography (CT), position-emission tomography (PET) and computed radiography (CR). Further still, they can be used for cathodoluminescence induced by electron beams for monitor screens as as TVs, computers, or any displays related to cathodolumienscence or electron beams. The radiation detection by detecting singlet oxygen produced by radiation is particularly useful for radiation detection in solutions such as water. In addition, the material and method can be used for biological sensing and detection, as well as for light detection and sensing.

In one aspect the present disclosure relates to a method for the detection of radiation, comprising contacting the disclosed Cu-Cy complex with a source of electromagnetic radiation.

In a further aspect the present disclosure relates to a method for detecting radiation, comprising:
 a) exposing the disclosed Cu-Cy compound to a source of radiation; and
 b) measuring the emission spectrum produced.

In a still further aspect the present disclosure relates to a method for detecting a source of radiation or for determining if a source of radiation is present, comprising:
 a) coating the surface of a substrate that is unaffected by radiation with the disclosed Cu-Cy compound;
 b) exposing the surface comprising the disclosed Cu-Cy compound to a site or object suspected of producing a source of radiation; and
 c) determining if the surface emits photoluminescence.
Photoluminescence Also disclosed herein is a method of producing photoluminescent lighting, comprising irradiating a compound having the formula:

$$Cu_3Cl(SR)_2$$

wherein R is —CH$_2$CH$_2$NH$_2$; with a source of electromagnetic radiation.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A method for detecting radiation, comprising:
 a) exposing a compound having the formula:

$$Cu_3Cl(SR)_2$$

wherein R is —CH$_2$CH$_2$NH$_2$ to a source of radiation; and
 b) measuring the emission spectrum produced.

2. The method according to claim 1, wherein the source of radiation is chosen from an X-ray source, a gamma-ray source, a beta-ray source, a source of proton emission, a source of electron emission, or a source of neutron emission.

3. The method according to claim 1, wherein the source of electromagnetic radiation is an X-ray source.

4. The method according to claim 1, wherein the source of electromagnetic radiation is a source of ultraviolet light.

5. The method according to claim 1, wherein the emission spectrum is measured at 605 nm, 633 nm, or both.

6. A method for detecting radiation, comprising:
 a) exposing a compound having the formula:

$$Cu_3Cl(SR)_2$$

wherein R is —CH$_2$CH$_2$NH$_2$ to a source of radiation; and
 b) measuring the amount of radiation produced.

7. The method according to claim 6, wherein the source of radiation is chosen from an X-ray source, a gamma-ray source, a beta-ray source, a source of proton emission, a source of electron emission, or a source of neutron emission.

8. The method according to claim 6, wherein the source of electromagnetic radiation is an X-ray source.

9. The method according to claim 6, wherein the source of electromagnetic radiation is a source of ultraviolet light.

10. The method according to claim 6, wherein the amount of radiation produced is determined by the emission spectrum measured at 605 nm, 633 nm, or both.

11. A method for detecting a source of radiation or for determining if a source of radiation is present, comprising:
 a) coating the surface of a substrate that is unaffected by radiation with the a radiation detecting compound having the formula:

$$Cu_3Cl(SR)_2$$

wherein R is —CH$_2$CH$_2$NH$_2$;
 b) exposing the surface comprising the radiation detecting compound to a site or object suspected of producing a source of radiation; and
 c) determining if the surface emits photoluminescence.

12. The method according to claim 11, wherein the source of radiation is chosen from an X-ray source, a gamma-ray source, a beta-ray source, a source of proton emission, a source of electron emission, or a source of neutron emission.

13. The method according to claim 11, wherein the source of electromagnetic radiation is an X-ray source.

14. The method according to claim 11, wherein the source of electromagnetic radiation is a source of ultraviolet light.

15. The method according to claim 11, further comprising recording the excitation and emission spectrum of the photoluminescence.

16. The method according to claim 11, wherein the emission spectrum is recorded at 607 nm, 633 nm or both.

* * * * *